(12) United States Patent
Heffernan et al.

(10) Patent No.: US 7,579,370 B2
(45) Date of Patent: Aug. 25, 2009

(54) FUSED HETEROCYCLES

(75) Inventors: Michele L. R. Heffernan, Worcester, MA (US); James M. Dorsey, Durham, NC (US); Qun Kevin Fang, Wellesley, MA (US); Robert J. Foglesong, Durham, NC (US); Seth C. Hopkins, Clinton, MA (US); Cyprian O. Ogbu, Durham, NC (US); Mustapha Soukri, Raleigh, NC (US); Kerry L. Spear, Concord, MA (US)

(73) Assignee: Sepracor Inc., Marlborough, MA (US)

( * ) Notice: Subject to any disclaimer, the term of this patent is extended or adjusted under 35 U.S.C. 154(b) by 0 days.

(21) Appl. No.: 11/833,903

(22) Filed: Aug. 3, 2007

(65) Prior Publication Data

US 2008/0004328 A1   Jan. 3, 2008

Related U.S. Application Data

(63) Continuation-in-part of application No. 11/825,093, filed on Jul. 2, 2007.

(60) Provisional application No. 60/806,391, filed on Jun. 30, 2006, provisional application No. 60/842,465, filed on Sep. 5, 2006, provisional application No. 60/914,293, filed on Apr. 26, 2007.

(51) Int. Cl.
| | |
|---|---|
| A61K 31/40 | (2006.01) |
| A61K 31/34 | (2006.01) |
| A61K 31/19 | (2006.01) |
| A01N 43/38 | (2006.01) |
| A01N 43/08 | (2006.01) |
| A01N 37/00 | (2006.01) |

(52) U.S. Cl. .................. 514/412; 514/469; 514/414; 514/557

(58) Field of Classification Search ............ 514/412, 514/414, 469, 557

See application file for complete search history.

(56) References Cited

U.S. PATENT DOCUMENTS

| | | | |
|---|---|---|---|
| 6,479,527 B1 * | 11/2002 | Barker et al. ............... | 514/367 |
| 6,576,653 B2 | 6/2003 | Du Bois | |
| 7,226,938 B2 | 6/2007 | Cai | |
| 2002/0183369 A1 | 12/2002 | Du Bois | |
| 2003/0195361 A1 | 10/2003 | Du Bois | |
| 2003/0215523 A1 | 11/2003 | Ozawa | |
| 2006/0235002 A1 | 10/2006 | Nagai | |
| 2007/0100135 A1 | 5/2007 | Riggs | |
| 2007/0142452 A1 * | 6/2007 | Banner et al. ............... | 514/414 |

FOREIGN PATENT DOCUMENTS

| | | |
|---|---|---|
| EP | 1391460 A1 | 2/2004 |
| WO | WO 99/40914 A1 * | 8/1999 |
| WO | WO 03/039540 A2 | 5/2003 |
| WO | WO 2004/022537 A2 | 3/2004 |
| WO | WO 2005/066135 A2 | 7/2005 |
| WO | WO 2006/004040 A1 | 1/2006 |
| WO | WO 2006/077412 A1 | 7/2006 |
| WO | WO 2007/039773 A1 * | 4/2007 |
| WO | WO 2007039773 A1 | 4/2007 |
| WO | WO 2007/068621 A1 | 6/2007 |

OTHER PUBLICATIONS

STN Registry File No. 67268-37-5. Registry File. Retrieved from STN 2008-03-17. One page.*
Bobosik et al. Synthesis of N-Phenylsulfonyl Protected Furo[3,2-b] Pyrroles, *Collect. Czech. Chem. Commun.* (vol. 59) pp. 499-502 (1994).
Cyranski et al. "Aromaticity of dihertero analogues of pentalene dianion. X-ray and ab initio studies of eight methyl furo[3,2-b]pyrrole-5-carboxylate derivatives and five methyl furo[2,3-b]pyrrole-5-carboxylate derivatives" *Tetrahedon* 57 8867-8873 (2001).
Dandarova, et al. "C NMR Spectra of Some Substituted Furo[3,2-b] pyrroles" *Magnetic Resonance in Chemistry*, vol. 28, 830-831 (1990).

(Continued)

*Primary Examiner*—Ardin Marschel
*Assistant Examiner*—Leslie A Royds
(74) *Attorney, Agent, or Firm*—Morgan, Lewis & Bockius, LLP

(57) ABSTRACT

This invention provides fused heterocycles having the formula:

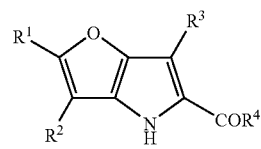

in which $R^1$ is a member selected from the group consisting of H, substituted or unsubstituted arylalkyl and substituted or unsubstituted heteroarylalkyl. $R^2$ is a member selected from the group consisting of H substituted or unsubstituted alkenyl, substituted or unsubstituted arylalkyl and substituted or unsubstituted heteroarylalkyl. $R^3$ is a member selected from the group consisting of H, $C_1$-$C_6$ substituted or unsubstituted alkyl, substituted or unsubstituted arylalkyl and substituted or unsubstituted heteroarylalkyl. $R^4$ is a member selected from OH and $O^-X^+$, in which $X^+$ is positive ion which is a member selected from organic positive ions and inorganic positive ions. Substituted or unsubstituted arylalkyl and substituted or unsubstituted heteroarylalkyl moieties have the formula:

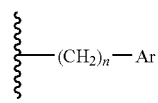

in which Ar is a member selected from the group consisting of substituted or unsubstituted aryl and substituted or unsubstituted heteroaryl. The index n is an integer from 1 to 4.

15 Claims, No Drawings

OTHER PUBLICATIONS

Ferguson et al. "N-Acetyl-5,6-Dihydrofuro[3,2-b]Pyrid-2-One, $C_9H_9NO_3$" *Cryst. Struct. Comm.* 5, 911 (1976).

Fisera et al. "Correlation of Kinetic Data of 1,3-Dipolar Cycloadditions of C-Benzoyl-N-Phenylnitrones With the Homo Energies of Furan Derivatives" *Collect. Czech. Chem. Commun.* vol. 46, 1504-1512 (1981).

Fisera et al. "Cycloadditions of C-Benzoyl-N-Phenylnitrone with Furocondensed Derivatives" *Collect. Czech. Chem. Commun.* vol. 48, 2421-2427 (1981).

Fukuda, et al. "Tensidols, New Potentiators of Antifungal Miconazole Activity, Produced by *Aspergillus niger* FKI-2342" *J. Antibiot* 59(8): 480-485 (2006).

Gross et al. "Direct Observation of 1-Azafulven-6-one and Annelated Derivatives" *J. Chem. Soc. Chem. Commun.* p. 360-361 (1982).

Hemetsberger et al. "Synthase und Thermolyse von α-Azidoacrylestern" *Monatshefte für Chemie*, 103, 194-204, (1972).

Ilyin et al. "Synthesis of Annelated Azaheterocycles Containing a 5-Carbamoylpyrazin-3-one Fragment by a Modification of the Four-Component Ugi Reaction" *Eur. J. Org. Chem.* 4670-4679 (2005).

Java et al. "Chimie Organique—Synthese de selnolo, furo et pyrrolpyrroles" *C. R. Acad. Sc. Paris*, t. 281 (Nov. 10, 1975) Serie C—793-795.

Koren et al. "Structure of a Furo[s,2-b]pyrrole Derivative" *Acta. Cryst.* C44, 2032-2033 (1988).

Kralovicova et al., "Electrophilic Substitution Reactions of Furo[3,2-b]Pyrrole Derivatives" *Collect. Czech. Chem. Commun.* (vol. 51) 106-111 (1986).

Krutosikova et al. "Addition and Cycloaddition Reactions of Furo[3,2-b]-Pyrroles and Their Benzo[b] Analogues: an NMR Study of Structure of Products" *Collect. Czech. Chem. Commun.* (vol. 53) 1770-1778 (1988).

Krutosikova et al. "Effect of microwave irradiation on reaction of furo[3,2-b]pyrrole and furo[2,3-b]pyrrole-2-carbeldehydes with some active methylene compounds" *ARKIVOC* (iii) 409-420 (2000).

Krutosikova et al. "Reactions of Ethyl 2-(4-Chlorophenyl)-4H-Furo[3,2-b]Pyrrole-5-Carboxylate" *Collect. Czech. Chem. Commun.* vol. 45, 2949-2957 (1980).

Krutosikova et al. "Reactions of furo[3,2-b]pyrroles and their benzol[b] analogues", *Chem Papers* 42 (1) 89-95 (1988).

Krutosikova et al. "Reactions of Methyl 2-Formylfuro[3,2-b]pyrrole-5-carboxylates" *Chem Papers* 50 (2)72-76 (1996).

Krutosikova et al. "Substituted 4-Benzylfuro [3,2-b] Pyrroles" *Collect. Czech. Chem. Commun.* (vol. 57) 1487-1494 (1992).

Krutosikova et al. "Substituted Vinyl Azides in the Synthesis of Condensed Nitrogen Heterocycles" *Chem Papers* 48 (4) 268-273 (1996).

Krutosikova et al. "Synthesis and reactions of 4-Oxiranylmethylfuro-[3,2-b]Pyrroles and their benzo derivatives" *Chem. of Heterocyclic Compounds* vol. 37, No. 12, 1511-1517 (2001).

Krutosikova et al. "Synthesis and reactions of Furo[2,3-b]pyrroles" *Molecules* (2) 69-79 (1997).

Krutosikova et al. "Synthesis and Reactions of Furocondensed Derivatives" *Collect. Czech. Chem. Commun.* (vol. 49) 65-70 (1984).

Krutosikova et al. "Synthesis and Reactions of Substituted Furo[3,2-b]Pyrrole Derivatives" *Collect. Czech. Chem. Commun.* (vol. 46) 2564-2572 (1981).

New et al. "The Thieno [3.2-c]pyridine and Furo[3,2-c]pyridine rings: New Pharmacophonres with Potential Antipsychotic Acivity" *J. Med. Chem* vol. 32, 1147-1156 (1989).

Ogawa et al. "Preparation of Oxygen-Bridged AZA[15]- and AZA[17]Annulene Dicarboxylates by Intramuscular Azide Cyclization" *Tetrahedon Letters*, vol. 29, No. 2, pp. 219-222, 1988.

Puterova et al. "Reaction of Substituted Furan-2-carboxaldehydes and Furo[b]pyrrole Type Aldehydes with Hippuric Acid" *Molecules* vol. 9, 11-21 (2004).

Puterova, et al. "Reactions of Substituted Furan-2-carboxaldehydes and Furo[b] pyrrole Type Aldehydes with Benzothiazolium Salts" *Molecules* vol. 9, 241-255 (2004).

Romanova et al. "DC Polarographic and UV Spectrometric Studies of Substituted Furo[3,2-b]- and Furo[2,3-b]Pyrroles" *Collect. Czech. Chem. Commun.* (vol. 66) 1615-1622 (2001).

Sleziak et al. "Furo[2,3-b]Pyrrole Derivatives, Syntheses and Reactions in the Furan and Pyrrole Ring" *Polish J. Chem.* vol. 74, 207-217 (2000).

Sleziak et al. "Reactions of Furo[2,3-b]Pyrrole and Furo[3,2-b]Pyrrole-Type Aldehydes" *Collect. Czech. Chem. Commun.* (vol. 64) 1135-1146 (1999).

Sorotskaya et al. "The Series of Substituted Butenolides and Butenolides, IV. 4-Arylidene (Heteroarylidene)-2-Butenolides" *Zhurnal Organicheskoi Khimiii*, vol. 25, No. 1, pp. 175-182 (1989).

Soth et al. "Recherches en série hétérocylique. XXIX. Sur des voies d'accés á des tghiéno, sélénolo, furo et pyrrolopyrroles[1]" *Can. J. Chem.* vol. 56, 1429-1434, (1978).

Welch et al. "Improved Synthesis of [3,2-b] and [2,3-b]-fused Selenolo-and Thienopyrroles, and of Furo[3,2-b]pyrrole" *Heterocyclic Communications* vol. 5, No. 4, 305-310 (1999).

* cited by examiner

FUSED HETEROCYCLES

CROSS-REFERENCES TO RELATED APPLICATIONS

The present application is a continuation-in-part of U.S. patent application Ser. No. 11/825,093, filed Jul. 2, 2007, which is related to U.S. Provisional Patent Application No. 60/806,391 filed on Jun. 30, 2006, U.S. Provisional Patent Application No. 60/842,465 filed on Sep. 5, 2006, and U.S. Provisional Patent Application No. 60/914,293 filed on Apr. 26, 2007 each of which is incorporated herein by reference in its entirety for all purposes.

FIELD OF THE INVENTION

This invention relates to enzyme inhibitors and methods of treating diseases and conditions, wherein modulation of D-amino acid oxidase activity, D-serine levels, D-serine oxidative products and NMDA receptor activity in the nervous system of a mammalian subject is effective, along with a reduction in undesirable side effects.

BACKGROUND OF THE INVENTION

The enzyme D-amino acid oxidase (DAAO) metabolizes D-amino acids, and in particular, metabolizes D-serine in vitro at physiological pH. DAAO is expressed in the mammalian brain and periphery. D-Serine's role as a neurotransmitter is important in the activation of the N-methyl-D-aspartate (NMDA) selective subtype of the glutamate receptor, an ion channel expressed in neurons, here denoted as NMDA receptor.

NMDA receptors mediate many physiological functions. NMDA receptors are complex ion channels containing multiple protein subunits that act either as binding sites for transmitter amino acids and/or as allosteric regulatory binding sites to regulate ion channel activity. D-serine, released by glial cells, has a distribution similar to NMDA receptors in the brain and acts as an endogenous ligand of the allosteric "glycine" site of these receptors (Mothet et al., *PNAS*, 97:4926 (2000)), the occupation of which is required for NMDA receptor operation. D-serine is synthesized in brain through serine racemase and degraded by D-amino oxidase (DAAO) after release.

Small organic molecules, which inhibit the enzymatic cycle of DAAO, may control the levels of D-serine, and thus influence the activity of the NMDA receptor in the brain. NMDA receptor activity is important in a variety of disease states, such as schizophrenia, psychosis, ataxia, ischemia, several forms of pain including neuropathic pain, and deficits in memory and cognition.

DAAO inhibitors may also control production of toxic metabolites of D-serine oxidation, such as hydrogen peroxide and ammonia. Thus, these molecules may influence the progression of cell loss in neurodegenerative disorders. Neurodegenerative diseases are diseases in which CNS neurons and/or peripheral neurons undergo a progressive loss of function, usually accompanied by (and perhaps caused by) a physical deterioration of the structure of either the neuron itself or its interface with other neurons. Such conditions include Parkinson's disease, Alzheimer's disease, Huntington's disease and neuropathic pain. N-methyl-D-aspartate (NMDA)-glutamate receptors are expressed at excitatory synapses throughout the central nervous system (CNS). These receptors mediate a wide range of brain processes, including synaptic plasticity, that are associated with certain types of memory formation and learning. NMDA-glutamate receptors require binding of two agonists to induce neurotransmission. One of these agonists is the excitatory amino acid L-glutamate, while the second agonist, at the so-called "strychnine-insensitive glycine site", is now thought to be D-serine. In animals, D-serine is synthesized from L-serine by serine racemase and degraded to its corresponding ketoacid by DAAO. Together, serine racemase and DAAO are thought to play a crucial role in modulating NMDA neurotransmission by regulating CNS concentrations of D-serine.

Known inhibitors of DAAO include benzoic acid, pyrrole-2-carboxylic acids, and indole-2-carboxylic acids, as described by Frisell, et al., *J. Biol. Chem.*, 223:75-83 (1956) and Parikh et al., *JACS*, 80:953 (1958). Indole derivatives and particularly certain indole-2-carboxylates have been described in the literature for treatment of neurodegenerative disease and neurotoxic injury. EP 396124 discloses indole-2-carboxylates and derivatives for treatment or management of neurotoxic injury resulting from a CNS disorder or traumatic event or in treatment or management of a neurodegenerative disease. Several examples of traumatic events that may result in neurotoxic injury are given, including hypoxia, anoxia, and ischemia, associated with perinatal asphyxia, cardiac arrest or stroke. Neurodegeneration is associated with CNS disorders such as convulsions and epilepsy. U.S. Pat. Nos. 5,373,018; 5,374,649; 5,686,461; 5,962,496 and 6,100,289, to Cugola, disclose treatment of neurotoxic injury and neurodegenerative disease using indole derivatives. None of the above references mention improvement or enhancement of learning, memory or cognition.

WO 03/039540 to Heefner et al. and U.S. patent application Nos. 2005/0143443 to Fang et al. and 2005/0143434 to Fang et al. disclose DAAO inhibitors, including indole-2-carboxylic acids, and methods of enhancing learning, memory and cognition as well as methods for treating neurodegenerative disorders. Patent application No. WO/2005/089753 discloses benzisoxazole analogs and methods of treating mental disorders, such as schizophrenia. However, a need for additional drug molecules that are effective in treating memory defects, impaired learning, loss of cognition, and other symptoms related to NMDA receptor activity, remains. The present invention addresses this and other needs.

SUMMARY OF THE INVENTION

The invention provides novel inhibitors of D-amino acid oxidase that are useful in the prevention and treatment of a variety of diseases and/or conditions including neurological disorders, pain, ataxia, and convulsion.

In a first aspect, the present invention provides a compound having a structure according to Formula (I):

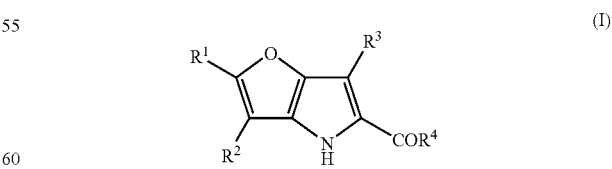

in which $R^1$ is H, substituted or unsubstituted arylalkyl or substituted or unsubstituted heteroarylalkyl. The symbol $R^2$ is represents H, substituted or unsubstituted alkenyl, substituted or unsubstituted arylalkyl or substituted or unsubstituted heteroarylalkyl. $R^3$ is H, $C_1$-$C_6$ substituted or unsubstituted alkyl, substituted or unsubstituted arylalkyl or substituted or unsubstituted heteroarylalkyl. The radical $R^4$ represents OH or $O^-X^+$, wherein $X^1$ is a positive ion which is a member selected from organic positive ions and inorganic positive ions. The invention also includes salts, hydrates, solvates and prodrugs of the compounds of Formula I.

In the context of Formula I, substituted or unsubstituted arylalkyl and substituted or unsubstituted heteroarylalkyl have the formula:

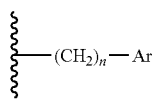

in which Ar is substituted or unsubstituted aryl or substituted or unsubstituted heteroaryl. The index n is an integer from 1 to 4.

In a preferred embodiment, the compound according to Formula I is incorporated into a pharmaceutical formulation along with one or more pharmaceutically acceptable diluent, excipient, carrier, etc. Those of skill in the art will recognize the overlap in the terms "diluent", "excipient" and "carrier".

In a further aspect the invention provides a method for treating or preventing a disease or condition which is a member selected from a neurological disorder, pain, ataxia and convulsion. The method includes administering to a subject in need thereof a therapeutically effective amount of a compound of Formula (I) or a pharmaceutically acceptable salt or solvate thereof.

DETAILED DESCRIPTION OF THE INVENTION

I. Definitions

Where substituent groups are specified by their conventional chemical formulae, written from left to right, they optionally encompass substituents resulting from writing the structure from right to left, e.g., —CH$_2$O— optionally also recites —OCH$_2$—.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl" with the difference that the heteroalkyl group, in order to qualify as an alkyl group, is linked to the remainder of the molecule through a carbon atom. Alkyl groups that are limited to hydrocarbon groups are termed "homoalkyl".

The term "alkenyl" by itself or as part of another substituent is used in its conventional sense, and refers to a radical derived from an alkene, as exemplified, but not limited by, substituted or unsubstituted vinyl and substituted or unsubstituted propenyl. Typically, an alkenyl group will have from 1 to 24 carbon atoms, with those groups having from 1 to 10 carbon atoms being generally preferred.

The term "alkylene" by itself or as part of another substituent means a divalent radical derived from an alkane, as exemplified, but not limited, by —CH$_2$CH$_2$CH$_2$CH$_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —CO$_2$R'— represents both —C(O)OR' and —OC(O)R'.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. A "cycloalkyl" or "heterocycloalkyl" substituent may be attached to the remainder of the molecule directly or through a linker, wherein the linker is preferably alkylene. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C$_1$-C$_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms selected from N, O, S, Si and B, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) optionally includes both aryl and heteroaryl rings as defined above. Thus, the term "arylalkyl" optionally includes those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") optionally include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O) NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O) CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: substituted or unsubstituted alkyl, substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O) NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'" and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'" and R"" groups when more than one of these groups is present.

Two of the substituents on adjacent atoms of the aryl or heteroaryl ring may optionally be replaced with a substituent of the formula —T—C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula —A—(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted (C$_1$-C$_6$)alkyl.

As used herein, the term "acyl" describes a substituent containing a carbonyl residue, C(O)R. Exemplary species for R include H, halogen, substituted or unsubstituted alkyl, substituted or unsubstituted aryl, substituted or unsubstituted heteroaryl, and substituted or unsubstituted heterocycloalkyl.

As used herein, the term "fused ring system" means at least two rings, wherein each ring has at least 2 atoms in common with another ring. "Fused ring systems may include aromatic as well as non aromatic rings. Examples of "fused ring systems" are naphthalenes, indoles, quinolines, chromenes and the like.

As used herein, the term "heteroatom" includes oxygen (O), nitrogen (N), sulfur (S) and silicon (Si), boron (B) and phosphorus (P).

The symbol "R" is a general abbreviation that represents a substituent group, e.g., one that is selected from substituted or unsubstituted alkyl, substituted or unsubstituted heteroalkyl, substituted or unsubstituted aryl, substituted or unsubstituted heteroaryl, and substituted or unsubstituted heterocycloalkyl groups.

The phrase "therapeutically effective amount" as used herein means that amount of a compound, material, or composition comprising a compound of the present invention which is effective for producing some desired therapeutic effect by inhibition of DAAO in at least a sub-population of cells in an animal and thereby blocking the biological consequences of that pathway in the treated cells, at a reasonable benefit/risk ratio applicable to any medical treatment.

The term "pharmaceutically acceptable salts" includes salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., *Journal of Pharmaceutical Science*, 66: 1-19 (1977)). Certain specific compounds of the present invention contain both basic and acidic functionalities that allow the compounds to be converted into either base or acid addition salts.

When a residue (such as $R^4$ in this application) is defined as "$O^-$", then the formula is meant to optionally include an organic or inorganic cationic counterion. Preferably, the resulting salt form of the compound is pharmaceutically acceptable.

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds, which are in a prodrug form. Prodrugs of the compounds described herein are those compounds that readily undergo chemical changes under physiological conditions to provide the compounds of the present invention. For instance, prodrugs for carboxylic acid analogs of the invention include a variety of esters. In an exemplary embodiment, the pharmaceutical compositions of the invention include a carboxylic acid ester. In another exemplary embodiment, the prodrug is suitable for treatment/prevention of those diseases and conditions that require the drug molecule to cross the blood brain barrier. In a preferred embodiment, the prodrug enters the brain, where it is converted into the active form of the drug molecule. In another example, a prodrug is used to enable an active drug molecule to reach the inside of the eye after topical application of the prodrug to the eye. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms ("polymorphs"). In general, all physical forms are of use in the methods contemplated by the present invention and are intended to be within the scope of the present invention. "Compound or a pharmaceutically acceptable salt, hydrate, polymorph or solvate of a compound" intends the inclusive meaning of "or", in that materials meeting more than one of the stated criteria are included, e.g., a material that is both a salt and a solvate is encompassed.

Certain compounds of the present invention possess asymmetric carbon atoms (optical centers) or double bonds; the racemates, diastereomers, geometric isomers and individual isomers are encompassed within the scope of the present invention. Optically active (R)— and (S)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are included.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

In the context of the present invention, compounds that are considered to possess activity as DAAO inhibitors are those displaying 50% inhibition of the enzymatic activity of DAAO ($IC_{50}$) at a concentration of not higher than about 100 µM, preferably, not higher than about 10 µM, more preferably not higher than about 1 µM and most preferably not higher than about 100 nM.

The term "neurological disorder" refers to any condition of the central or peripheral nervous system of a mammal. The term "neurological disorder" includes neurodegenerative diseases (e.g., Alzheimer's disease, Parkinson's disease and amyotrophic lateral sclerosis), neuropsychiatric diseases (e.g. Schizophrenia and anxieties, such as general anxiety disorder). Exemplary neurological disorders include MLS (cerebellar ataxia), Huntington's disease, Down syndrome, multi-infarct dementia, status epilecticus, contusive injuries (e.g. spinal cord injury and head injury), viral infection induced neurodegeneration, (e.g. AIDS, encephalopathies), epilepsy, benign forgetfulness, closed head injury, sleep disorders, depression (e.g., bipolar disorder), dementias, movement disorders, psychoses, alcoholism, post-traumatic stress disorder and the like. "Neurological disorder" also includes any condition associated with the disorder. For instance, a method of treating a neurodegenerative disorder includes methods of treating loss of memory and/or loss of cognition associated with a neurodegenerative disorder. Such method would also include treating or preventing loss of neuronal function characteristic of neurodegenerative disorder.

"Pain" is an unpleasant sensory and emotional experience. Pain classifications have been based on duration, etiology or pathophysiology, mechanism, intensity, and symptoms. The term "pain" as used herein refers to all categories of pain, including pain that is described in terms of stimulus or nerve response, e.g., somatic pain (normal nerve response to a noxious stimulus) and neuropathic pain (abnormal response of a injured or altered sensory pathway, often without clear noxious input); pain that is categorized temporally, e.g., chronic pain and acute pain; pain that is categorized in terms of its severity, e.g., mild, moderate, or severe; and pain that is a symptom or a result of a disease state or syndrome, e.g., inflammatory pain, cancer pain, AIDS pain, arthropathy, migraine, trigeminal neuralgia, cardiac ischaemia, and diabetic peripheral neuropathic pain (see, e.g., Harrison's Principles of Internal Medicine, pp. 93-98 (Wilson et al., eds., 12th ed. 1991); Williams et al., *J. of Med. Chem.* 42: 1481-1485 (1999), herein each incorporated by reference in their entirety). "Pain" is also meant to include mixed etiology pain, dual mechanism pain, allodynia, causalgia, central pain, hyperesthesia, hyperpathia, dysesthesia, and hyperalgesia.

"Somatic" pain, as described above, refers to a normal nerve response to a noxious stimulus such as injury or illness, e.g., trauma, burn, infection, inflammation, or disease process such as cancer, and includes both cutaneous pain (e.g., skin, muscle or joint derived) and visceral pain (e.g., organ derived).

"Neuropathic pain" is a heterogeneous group of neurological conditions that result from damage to the nervous system. "Neuropathic" pain, as described above, refers to pain resulting from injury to or dysfunctions of peripheral and/or central sensory pathways, and from dysfunctions of the nervous system, where the pain often occurs or persists without an obvious noxious input. This includes pain related to peripheral neuropathies as well as central neuropathic pain. Common types of peripheral neuropathic pain include diabetic neuropathy (also called diabetic peripheral neuropathic pain, or DN, DPN, or DPNP), post-herpetic neuralgia (PHN), and trigeminal neuralgia (TGN). Central neuropathic pain, involving damage to the brain or spinal cord, can occur following stroke, spinal cord injury, and as a result of multiple sclerosis. Other types of pain that are meant to be included in the definition of neuropathic pain include pain from spinal cord injury, neuropathic cancer pain, HIV/AIDS induced pain, phantom limb pain, and complex regional pain syndrome. In a preferred embodiment, the compounds of the invention are of use for treating neuropathic pain. An exemplary compound of use in this embodiment is a compound according to Formula I in which each of $R^1$-$R^3$ is hydrogen, and $R^4$ is selected such that the compound is a free acid or salt thereof.

Common clinical features of neuropathic pain include sensory loss, allodynia (non-noxious stimuli produce pain), hyperalgesia and hyperpathia (delayed perception, summation, and painful aftersensation). Pain is often a combination of nociceptive and neuropathic types, for example, mechanical spinal pain and radiculopathy or myelopathy.

"Acute pain", is the normal, predicted physiological response to a noxious chemical, thermal or mechanical stimulus typically associated with invasive procedures, trauma and disease. It is generally time-limited, and may be viewed as an appropriate response to a stimulus that threatens and/or produces tissue injury. "Acute pain", as described above, refers to pain which is marked by short duration or sudden onset.

"Chronic pain" occurs in a wide range of disorders, for example, trauma, malignancies and chronic inflammatory diseases such as rheumatoid arthritis. Chronic pain usually lasts more than about six months. In addition, the intensity of chronic pain may be disproportionate to the intensity of the noxious stimulus or underlying process. "Chronic pain", as described above, refers to pain associated with a chronic disorder, or pain that persists beyond resolution of an underlying disorder or healing of an injury, and that is often more intense than the underlying process would predict. It may be subject to frequent recurrence.

"Inflammatory pain" is pain in response to tissue injury and the resulting inflammatory process. Inflammatory pain is adaptive in that it elicits physiologic responses that promote healing. However, inflammation may also affect neuronal function. Inflammatory mediators, including $PGE_2$ induced by the COX2 enzyme, bradykinins, and other substances, bind to receptors on pain-transmitting neurons and alter their function, increasing their excitability and thus increasing pain sensation. Much chronic pain has an inflammatory component. "Inflammatory pain", as described above, refers to pain which is produced as a symptom or a result of inflammation or an immune system disorder.

"Visceral pain", as described above, refers to pain which is located in an internal organ.

"Mixed etiology" pain, as described above, refers to pain that contains both inflammatory and neuropathic components.

"Dual mechanism" pain, as described above, refers to pain that is amplified and maintained by both peripheral and central sensitization.

"Causalgia", as described above, refers to a syndrome of sustained burning, allodynia, and hyperpathia after a traumatic nerve lesion, often combined with vasomotor and sudomotor dysfunction and later trophic changes.

"Central" pain, as described above, refers to pain initiated by a primary lesion or dysfunction in the central nervous system.

"Hyperesthesia", as described above, refers to increased sensitivity to stimulation, excluding the special senses.

"Hyperpathia", as described above, refers to a painful syndrome characterized by an abnormally painful reaction to a stimulus, especially a repetitive stimulus, as well as an increased threshold. It may occur with allodynia, hyperesthesia, hyperalgesia, or dysesthesia.

"Dysesthesia", as described above, refers to an unpleasant abnormal sensation, whether spontaneous or evoked. Special cases of dysesthesia include hyperalgesia and allodynia, "Hyperalgesia", as described above, refers to an increased response to a stimulus that is normally painful. It reflects increased pain on suprathreshold stimulation.

"Allodynia", as described above, refers to pain due to a stimulus that does not normally provoke pain.

The term "pain" includes pain resulting from dysfunction of the nervous system: organic pain states that share clinical features of neuropathic pain and possible common pathophysiology mechanisms, but are not initiated by an identifiable lesion in any part of the nervous system.

The term "Diabetic Peripheral Neuropathic Pain" (DPNP, also called diabetic neuropathy, DN or diabetic peripheral neuropathy) refers to chronic pain caused by neuropathy associated with diabetes mellitus. The classic presentation of DPNP is pain or tingling in the feet that can be described not only as "burning" or "shooting" but also as severe aching pain. Less commonly, patients may describe the pain as itching, tearing, or like a toothache. The pain may be accompanied by allodynia and hyperalgesia and an absence of symptoms, such as numbness.

The term "Post-Herpetic Neuralgia", also called "Postherpetic Neuralgia" (PHN), is a painful condition affecting nerve fibers and skin. It is a complication of shingles, a second outbreak of the varicella zoster virus (VZV), which initially causes chickenpox.

The term "neuropathic cancer pain" refers to peripheral neuropathic pain as a result of cancer, and can be caused directly by infiltration or compression of a nerve by a tumor, or indirectly by cancer treatments such as radiation therapy and chemotherapy (chemotherapy-induced neuropathy).

The term "HIV/AIDS peripheral neuropathy" or "HIV/AIDS-related neuropathy" refers to peripheral neuropathy caused by HIV/AIDS, such as acute or chronic inflammatory demyelinating neuropathy (AIDP and CIDP, respectively), as well as peripheral neuropathy resulting as a side effect of drugs used to treat HIV/AIDS.

The term "Phantom Limb Pain" refers to pain appearing to come from where an amputated limb used to be. Phantom limb pain can also occur in limbs following paralysis. It is usually chronic in nature. It is similar in nature to the limb pain experienced by patients with paralysis following spinal cord injury.

The term "Trigeminal Neuralgia" (TN) refers to a disorder of the fifth cranial (trigeminal) nerve that causes episodes of intense, stabbing, electric-shock-like pain in the areas of the face where the branches of the nerve are distributed (lips, eyes, nose, scalp, forehead, upper jaw, and lower jaw). It is also known as the "suicide disease".

The term "Complex Regional Pain Syndrome (CRPS)," formerly known as Reflex Sympathetic Dystrophy (RSD), is a chronic pain condition. The key symptom of CRPS is continuous, intense pain out of proportion to the severity of the injury, which gets worse rather than better over time. CRPS is divided into type 1, which includes conditions caused by tissue injury other than peripheral nerve, and type 2, in which the syndrome is provoked by major nerve injury, and is sometimes called causalgia.

The term "Fibromyalgia" refers to a chronic condition characterized by diffuse or specific muscle, joint, or bone pain, along with fatigue and a range of other symptoms. Previously, fibromyalgia was known by other names such as fibrositis, chronic muscle pain syndrome, psychogenic rheumatism and tension myalgias.

The term "convulsion" refers to a CNS disorder and is used interchangeably with "seizure," although there are many types of seizure, some of which have subtle or mild symptoms instead of convulsions. Seizures of all types may be caused by disorganized and sudden electrical activity in the brain. Convulsions are a rapid and uncontrollable shaking. During convulsions, the muscles contract and relax repeatedly.

II. Introduction

The present invention relates to novel inhibitors of the enzyme D-amino acid oxidase. These compounds are useful for treating or preventing any disease and/or condition, wherein modulation of D-serine levels, and/or its oxidative products, is effective in ameliorating symptoms. Inhibition of the enzyme can lead to increases in D-serine levels and a reduction in the formation of toxic D-serine oxidation products. Thus, the invention provides methods for the treatment or prevention of neurological disorders. For example, the invention provides methods of enhancing learning, memory and/or cognition, for treating or preventing loss of memory and/or cognition associated with neurodegenerative diseases (e.g., Alzheimer's disease) and for preventing loss of neuronal function characteristic of neurodegenerative diseases. Further, methods are provided for the treatment or prevention of pain, ataxia, and convulsion.

III. Compositions

A. Fused Heterocycles

The heterocyclic inhibitors of the invention are characterized by a variety of core-moieties.

In a first aspect, the present invention provides a compound having a structure according to Formula (I):

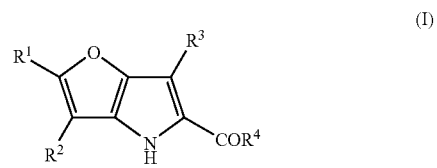

in which $R^1$ is H, substituted or unsubstituted arylalkyl or substituted or unsubstituted heteroarylalkyl. The symbol $R^2$ is represents H, substituted or unsubstituted alkenyl, substituted or unsubstituted arylalkyl or substituted or unsubstituted heteroarylalkyl. $R^3$ is H, $C_1$-$C_6$ substituted or unsubstituted alkyl, substituted or unsubstituted arylalkyl or substituted or unsubstituted heteroarylalkyl. The radical $R^4$ is OH or $O^-X^-$, wherein $X^+$ is positive ion which is a member selected from organic positive ions and inorganic positive ions. The invention also includes salts, hydrates, solvates and prodrugs of the compounds of Formula I.

In the context of Formula I, substituted or unsubstituted arylalkyl and substituted or unsubstituted heteroarylalkyl have the formula:

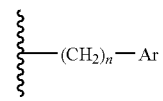

in which Ar is substituted or unsubstituted aryl or substituted or unsubstituted heteroaryl. The index n is an integer from 1 to 4.

In a preferred embodiment, the compound according to Formula I is incorporated into a pharmaceutical formulation along with one or more pharmaceutically acceptable diluent, excipient, carrier, etc. Those of skill will recognize that there is overlap between the terms "diluent", "excipient" and "carrier".

1. Synthesis of Fused Furan Pyrrole Analogs

Exemplary fused furan pyrrole analogs of the present invention are prepared using a procedure such as those outlined in Schemes 1, 2 and 3 below.

Scheme 1

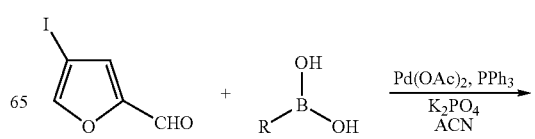

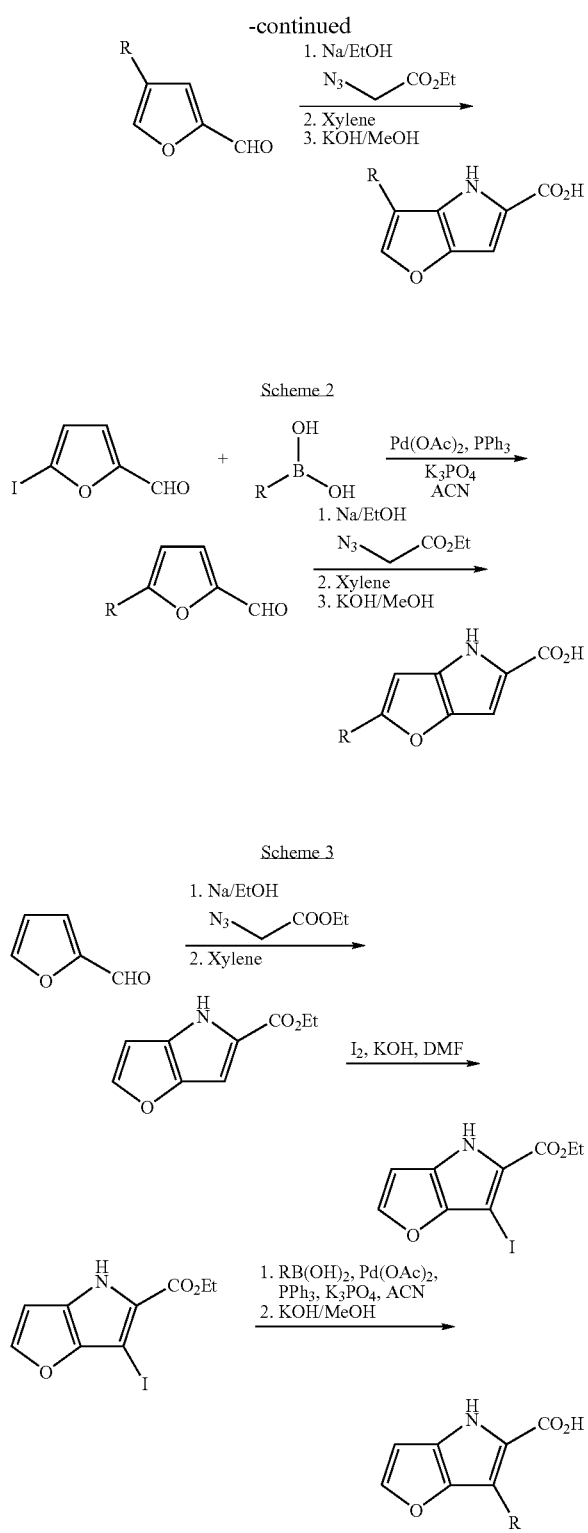

The fused furan pyrrole derivatives of the invention may be prepared by Suzuki coupling of a halogenated furan aldehyde and an appropriate boronic acid. Condensation of the resulting furan intermediate and 2-azidoacetate, followed by cyclization and saponification of the ester group affords the desired carboxylic acid analog (Schemes 1 and 2). Similarly, Suzuki coupling of a halogenated 4H-furo[3,2-b]pyrrole-5-carboxylic acid ester, followed by saponification, affords the desired carboxylic acid analog (Scheme 3).

C. Pharmaceutical Compositions

While compounds of the present invention can be administered as the raw chemical, it is preferable to present them as a pharmaceutical composition. According to a further aspect, the present invention provides a pharmaceutical composition comprising a compound of Formula (I) or a pharmaceutically acceptable salt, hydrate or solvate thereof, together with one or more pharmaceutical carrier and optionally one or more other therapeutic ingredients. The carrier(s) are "acceptable" in the sense of being compatible with the other ingredients of the formulation and not deleterious to the recipient thereof. The term "pharmaceutically acceptable carrier" includes vehicles, diluents, excipients and other elements appropriate for incorporation into a pharmaceutical formulation.

The formulations include those suitable for oral, parenteral (including subcutaneous, intradermal, intramuscular, intravenous and intraarticular), rectal and topical (including dermal, buccal, sublingual and intraocular) administration, as well as those for administration by inhalation. The most suitable route may depend upon the condition and disorder of the recipient. The formulations may conveniently be presented in unit dosage form and may be prepared by any of the methods well known in the art of pharmacy. All methods include the step of bringing into association a compound or a pharmaceutically acceptable salt or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation. Oral formulations are well known to those skilled in the art, and general methods for preparing them are found in any standard pharmacy school textbook, for example, Remington: The Science and Practice of Pharmacy., A. R. Gennaro, ed. (1995), the entire disclosure of which is incorporated herein by reference.

Pharmaceutical compositions containing compounds of Formula (I) may be conveniently presented in unit dosage form and prepared by any of the methods well known in the art of pharmacy. Preferred unit dosage formulations are those containing an effective dose, or an appropriate fraction thereof, of the active ingredient, or a pharmaceutically acceptable salt thereof. The magnitude of a prophylactic or therapeutic dose typically varies with the nature and severity of the condition to be treated and the route of administration. The dose, and perhaps the dose frequency, will also vary according to the age, body weight and response of the individual patient. In general, the total daily dose ranges from about 0.1 mg per day to about 7000 mg per day, preferably about 1 mg per day to about 100 mg per day, and more preferably, about 25 mg per day to about 50 mg per day, in single or divided doses. In some embodiments, the total daily dose may range from about 50 mg to about 500 mg per day, and preferably, about 100 mg to about 500 mg per day. It is further recommended that children, patients over 65 years old, and those with impaired renal or hepatic function, initially receive low doses and that the dosage is titrated based on individual responses and/or blood levels. It may be necessary to use dosages outside these ranges in some cases, as will be apparent to those in the art. Further, it is noted that the clinician or treating physician knows how and when to interrupt, adjust or terminate therapy in conjunction with individual patient's response.

It should be understood that in addition to the ingredients particularly mentioned above, the formulations of this invention may include other agents conventional in the art having regard to the type of formulation in question, for example those suitable for oral administration may include flavoring agents.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compressing or molding the compound of Formula (I), optionally using one or more additional ingredient. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein. Oral and parenteral sustained release drug delivery systems are well known to those skilled in the art, and general methods of achieving sustained release of orally or parenterally administered drugs are found, for example, in Remington: The Science and Practice of Pharmacy, pages 1660-1675 (1995).

Formulations for parenteral administration include aqueous and non-aqueous sterile injection solutions which may contain anti-oxidants, buffers, bacteriostats and solutes which render the formulation isotonic with the blood of the intended recipient. Formulations for parenteral administration also include aqueous and non-aqueous sterile suspensions, which may include suspending agents and thickening agents. The formulations may be presented in unit-dose or multi-dose containers, for example sealed ampoules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described. Formulations for rectal administration may be presented as a suppository with the usual carriers such as cocoa butter or polyethylene glycol. Formulations for topical administration in the mouth, for example, buccally or sublingually, include lozenges comprising the active ingredient in a flavored basis such as sucrose and acacia or tragacanth, and pastilles comprising the active ingredient in a basis such as gelatin and glycerin or sucrose and acacia.

The pharmaceutically acceptable carrier may take a wide variety of forms, depending on the route desired for administration, for example, oral or parenteral (including intravenous). In preparing the composition for oral dosage form, any of the usual pharmaceutical media may be employed, such as, water, glycols, oils, alcohols, flavoring agents, preservatives, and coloring agents in the case of oral liquid preparation, including suspension, elixirs and solutions. Carriers such as starches, sugars, microcrystalline cellulose, diluents, granulating agents, lubricants, binders and disintegrating agents may be used in the case of oral solid preparations such as powders, capsules and caplets, with the solid oral preparation being preferred over the liquid preparations. Preferred solid oral preparations are tablets or capsules, because of their ease of administration. If desired, tablets may be coated by standard aqueous or nonaqueous techniques. Oral and parenteral sustained release dosage forms may also be used.

Exemplary formulations, are well known to those skilled in the art, and general methods for preparing them are found in any standard pharmacy school textbook, for example, Remington, THE SCIENCE AND PRACTICE OF PHARMACY, 21st Ed., Lippincott.

Since one aspect of the present invention contemplates the treatment of the disease/conditions with a combination of pharmaceutically active agents that may be administered separately, the invention further relates to combining separate pharmaceutical compositions in kit form. The kit comprises two separate pharmaceutical compositions: a compound of the present invention, and a second pharmaceutical compound. The kit comprises a container for containing the separate compositions such as a divided bottle or a divided foil packet. Additional examples of containers include syringes, boxes, bags, and the like. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc . . . Second Week, Monday, Tuesday, . . . " etc. Other variations of memory aids will be readily apparent. A "daily dose" can be a single tablet or capsule or several pills or capsules to be taken on a given day. Also, a daily dose of a compound of the present invention can consist of one tablet or capsule, while a daily dose of the second compound can consist of several tablets or capsules and vice versa. The memory aid should reflect this and aid in correct administration of the active agents.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that have been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

IV. Methods

A. Methods for Treatment or Prevention

In a further aspect the invention provides a method for treating or preventing a disease or condition which is a member selected from a neurological disorder, pain, ataxia and convulsion. The method includes administering to a subject in need thereof a therapeutically effective amount of a compound of Formula (I) or a pharmaceutically acceptable salt, hydrate, prodrug or solvate thereof:

In an exemplary embodiment, the subject is preferably not in need of treatment for a condition, which is a member selected from a $H_4$-receptor mediated disease, a monocyte chemoattractant protein-1 (MCP-1) receptor mediated disease, type-2 diabetes, insulin resistance, syndrome X, hyperinsulinaemia, hyperglucagonaemia, cardiac ischemia, obesity, artherosclerosis, diabetic neuropathy, diabetic nephropathy, diabetic retinopathy, cataracts, hypercholesterolemia, hypertriglyceridemia, hyperlipidemia, hyperglycemia, hypertension, tissue ischemia and myocardial ischemia.

In another embodiment, the subject is preferably not in need of inhibiting glycogen phosphorylase.

Subjects for treatment according to the present invention include humans (patients) and other mammals in need of therapy for the stated condition.

Compounds of the invention possess unique pharmacological characteristics with respect to inhibition of DAAO and influence the activity of the NMDA receptor in the brain, particularly by controlling the levels of D-serine. Therefore, these compounds are effective in treating conditions and disorders (especially CNS-related disorders), which are modulated by DAAO, D-serine and/or NMDA receptor activity. In one embodiment, compounds of the invention are associated with diminished side effects compared to administration of the current standards of treatment.

Accordingly, the present invention relates to methods for increasing the concentration of D-serine and/or decreasing the concentration of toxic products of D-serine oxidation by DAAO in a mammal. Each of the methods comprises administering to a subject in need thereof a therapeutically effective amount of a compound of the invention, for example those of Formula (I), or a pharmaceutically acceptable salt, hydrate, prodrug or solvate thereof.

Compounds of the invention are typically more selective than known DAAO inhibitors, including indole-2-carboxylates, and demonstrate higher selectivity for DAAO inhibition relative to binding at the NMDA receptor's D-serine binding site. The compounds also exhibit an advantageous profile of activity including good bioavailability. Accordingly, they offer advantages over many art-known methods for treating disorders modulated by DAAO, D-serine or NMDA receptor activity. For example, unlike conventional antipsychotic therapeutics, DAAO inhibitors can produce a desirable reduction in the cognitive symptoms of schizophrenia. Conventional antipsychotics often produce undesirable side effects, including tardive dyskinesia (irreversible involuntary movement disorder), extra pyramidal symptoms, and akathesia, and these may be reduced or eliminated by administering compounds of the invention.

Compounds of the present invention may also be used in conjunction with therapy involving administration of D-serine or an analog thereof, such as a salt of D-serine, an ester of D-serine, alkylated D-serine, D-cycloserine or a precursor of D-serine, or can be used in conjunction with therapy involving administration of antipsychotics, antidepressants, psychostimulants, and/or Alzheimer's disease therapeutics.

The compounds of the invention may also be used in conjunction with therapy involving administration of antipsychotics (for treating schizophrenia and other psychotic conditions), psychostimulants (for treating attention deficit disorder, depression, or learning disorders), antidepressants, nootropics (for example, piracetam, oxiracetam or aniracetam), acetylcholinesterase inhibitors (for example, the physostigmine related compounds, tacrine or donepezil), GABA analogs (e.g., gabapentin) or GABA receptor modulators, Alzheimer's disease therapeutics (e.g., nemantine hydrochloride) and/or analgesics (for treating of persistant or chronic pain, e.g. neuropathic pain). Such methods for conjoint therapies are included within the invention.

Conditions and Disorders

In one embodiment, the compounds of the present invention are useful for the treatment of neurological disorders, pain (e.g., neuropathic pain), ataxia and convulsion. Neurological disorders include neurodegenerative diseases (e.g., Alzheimers disease) and neuropsychiatric disorders (e.g., schizophrenia).

Neuropsychiatric Disorders

Neuropsychiatric disorders include schizophrenia, autism, and attention deficit disorder. Clinicians recognize a distinction among such disorders, and there are many schemes for categorizing them. The Diagnostic and Statistical Manual of Mental Disorders, Revised, Fourth Ed., (DSM-IV-R), published by the American Psychiatric Association, provides a standard diagnostic system upon which persons of skill rely, and is incorporated herein by reference. According to the framework of the DSM-IV, the mental disorders of Axis I include: disorders diagnosed in childhood (such as Attention Deficit Disorder (ADD) and Attention Deficit-Hyperactivity Disorder (ADHD)) and disorders diagnosed in adulthood. The disorders diagnosed in adulthood include (1) schizophrenia and psychotic disorders; (2) cognitive disorders; (3) mood disorders; (4) anxiety related disorders; (5) eating disorders; (6) substance related disorders; (7) personality disorders; and (8) "disorders not yet included" in the scheme.

ADD and ADHD are disorders that are most prevalent in children and are associated with increased motor activity and a decreased attention span. These disorders are commonly treated by administration of psychostimulants such as methylphenidate and dextroamphetamine sulfate.

The compounds (and their mixtures) of the present invention are also effective for treating disruptive behavior disorders, such as attention deficit disorder (ADD) and attention deficit disorder/hyperactivity (ADHD), which is in accordance with its accepted meaning in the art, as provided in the DSM-IV-TR™. These disorders are defined as affecting one's behavior resulting in inappropriate actions in learning and social situations. Although most commonly occurring during childhood, disruptive behavior disorders may also occur in adulthood.

Schizophrenia represents a group of neuropsychiatric disorders characterized by dysfunctions of the thinking process, such as delusions, hallucinations, and extensive withdrawal of the patient's interests from other people. Approximately one percent of the worldwide population is afflicted with schizophrenia, and this disorder is accompanied by high morbidity and mortality rates. So-called negative symptoms of schizophrenia include affect blunting, anergia, alogia and social withdrawal, which can be measured using SANS (Andreasen, 1983, Scales for the Assessment of Negative Symptoms (SANS), Iowa City, Iowa). Positive symptoms of schizophrenia include delusion and hallucination, which can be measured using PANSS (Positive and Negative Syndrome Scale) (Kay et al., 1987, *Schizophrenia Bulletin* 13:261-276). Cognitive symptoms of schizophrenia include impairment in obtaining, organizing, and using intellectual knowledge which can be measured by the Positive and Negative Syndrome Scale-cognitive subscale (PANSS-cognitive subscale) (Lindenmayer et al., 1994, *J. Nerv. Ment. Dis.* 182:631-638) or with cognitive tasks such as the Wisconsin Card Sorting Test. Conventional antipsychotic drugs, which act on the dopamine $D_2$ receptor, can be used to treat the positive symptoms of schizophrenia, such as delusion and hallucination. In general, conventional antipsychotic drugs and atypical antipsychotic drugs, which act on the dopamine $D_2$ and $5HT_2$ serotonin receptor, are limited in their ability to treat cognitive deficits and negative symptoms such as affect blunting (i.e., lack of facial expressions), anergia, and social withdrawal.

Disorders treatable with the compounds of the present invention include, but are not limited to, depression, bipolar disorder, chronic fatigue disorder, seasonal affective disorder, agoraphobia, generalized anxiety disorder, phobic anxiety, obsessive compulsive disorder (OCD), panic disorder, acute stress disorder, social phobia, posttraumatic stress disorder, premenstrual syndrome, menopause, perimenopause and male menopause.

Compounds and compositions of the present invention are also effective for treating eating disorders. Eating disorders are defined as a disorder of one's appetite or eating habits or of inappropriate somatotype visualization. Eating disorders include, but are not limited to, anorexia nervosa; bulimia nervosa, obesity and cachexia.

In addition to their beneficial therapeutic effects, compounds of the present invention provide the additional benefit of avoiding one or more of the adverse effects associated with conventional mood disorder treatments. Such side effects include, for example, insomnia, breast pain, weight gain, extrapyramidal symptoms, elevated serum prolactin levels and sexual dysfunction (including decreased libido, ejaculatory dysfunction and anorgasmia).

Learning, Memory and Cognition

Generally, compounds of the invention can be used for improving or enhancing learning and memory. Patients, who may benefit from such treatment, include those exhibiting symptoms of dementia or learning and memory loss. Individuals with an amnesic disorder are impaired in their ability to learn new information or are unable to recall previously learned information or past events. The memory deficit is most apparent on tasks to require spontaneous recall and may also be evident when the examiner provides stimuli for the person to recall at a later time. The memory disturbance must be sufficiently severe to cause marked impairment in social or occupational functioning and must represent a significant decline from a previous level of functioning. The memory deficit may be age-related or the result of disease or other cause. Dementia is characterized by multiple clinically significant deficits in cognition that represent a significant change from a previous level of functioning, including memory impairment involving inability to learn new material or forgetting of previously learned material. Memory can be formally tested by measuring the ability to register, retain, recall and recognize information. A diagnosis of dementia also requires at least one of the following cognitive disturbances: aphasia, apraxia, agnosia or a disturbance in executive functioning. These deficits in language, motor performance, object recognition and abstract thinking, respectively, must be sufficiently severe in conjunction with the memory deficit to cause impairment in occupational or social functioning and must represent a decline from a previously higher level of functioning.

Compounds of the invention are useful for preventing loss of neuronal function, which is characteristic of neurodegenerative diseases. Therapeutic treatment with a compound of the invention improves and/or enhances memory, learning and cognition. In one embodiment, the compounds of the invention can be used to treat a neurodegenerative disease such as Alzheimer's, Huntington's disease, Parkinson's disease and amyotrophic lateral sclerosis, as well as MLS (cerebellar ataxia), Down syndrome, multi-infarct dementia, status epilecticus, contusive injuries (e.g. spinal cord injury and head injury), viral infection induced neurodegeneration, (e.g. AIDS, encephalopathies), epilepsy, benign forgetfulness, and closed head injury.

Compounds of the invention are useful for treating or preventing loss of memory and/or cognition associated with a neurodegenerative disease. The compounds also ameliorate cognitive dysfunctions associated with aging and improve catatonic schizophrenia Alzheimer's disease is manifested as a form of dementia that typically involves mental deterioration, reflected in memory loss, confusion, and disorientation. In the context of the present invention, dementia is defined as a syndrome of progressive decline in multiple domains of cognitive function, eventually leading to an inability to maintain normal social and/or occupational performance. Early symptoms include memory lapses and mild but progressive deterioration of specific cognitive functions, such as language (aphasia), motor skills (apraxia) and perception (agnosia). The earliest manifestation of Alzheimer's disease is often memory impairment, which is required for a diagnosis of dementia in both the National Institute of Neurological and Communicative Disorders and Stroke-Alzheimer's Disease-and the Alzheimer's Disease and Related Disorders Association (NINCDS-ADRDA) criteria (McKhann et al., 1984, Neurology 34:939-944), which are specific for Alzheimer's disease, and the American Psychiatric Association's Diagnostic and Statistical Manual of Mental Disorders, Fourth Edition (DSM-IV) criteria, which are applicable for all forms of dementia. The cognitive function of a patient may also be assessed by the Alzheimer's disease Assessment Scale-cognitive subscale (ADAS-cog; Rosen et al., 1984, *Am. J. Psychiatry* 141 :1356-1364). Alzheimer's disease is typically treated by acetylcholine esterase inhibitors such as tacrine hydrochloride or donepezil. Unfortunately, the few forms of treatment for memory loss and impaired learning available at present are not considered effective enough to make any significant difference to a patient, and there is currently a lack of a standard nootropic drug for use in such treatment.

Other conditions that are manifested as deficits in memory and learning include benign forgetfulness and closed head injury. Benign forgetfulness refers to a mild tendency to be unable to retrieve or recall information that was once registered, learned, and stored in memory (e.g., an inability to remember where one placed one's keys or parked one's car). Benign forgetfulness typically affects individuals after 40 years of age and can be recognized by standard assessment instruments such as the Wechsler Memory Scale. Closed head injury refers to a clinical condition after head injury or trauma. Such a condition, which is characterized by cognitive and memory impairment, can be diagnosed as "amnestic disorder due to a general medical condition" according to DSM-IV.

Compounds and compositions of the invention are also effective for treating cerebral function disorders. The term cerebral function disorder, as used herein, includes cerebral function disorders involving intellectual deficits, and may be exemplified by senile dementia, Alzheimer's type dementia, memory loss, amnesia/amnestic syndrome, epilepsy, disturbances of consciousness, coma, lowering of attention, speech disorders, Parkinson's disease and autism.

Pain

The compounds of the invention are useful to treat any kind of acute or chronic pain. In a preferred embodiment, the compounds of the invention are useful to treat chronic pain. In a particularly preferred embodiment, the compounds of the invention are useful to treat neuropathic pain. The term neuropathic "pain" includes central neuropathic pain, involving damage to the brain or spinal cord, such as may occur following stroke, spinal cord injury, and as a result of multiple sclerosis. It also includes peripheral neuropathic pain, which includes diabetic peripheral neuropathic pain, post-herpetic neuralgia (PHN), and trigeminal neuralgia (TN). It also includes dysfunctions of the nervous system such as Complex Regional Pain Syndrome (CRPS), formerly known as Reflex Sympathetic Dystrophy (RSD), and causalgia, and neuropathic pain symptoms such as sensory loss, allodynia, hyperalgesia and hyperpathia. It further includes mixed nociceptive and neuropathic pain types, for example, mechanical spinal pain and radiculopathy or myelopathy, and the treatment of chronic pain conditions such as fibromyalgia, lower back pain and neck pain due to spinal nerve root compression, neuropathic cancer pain, HIV/AIDS induced pain, and phantom limb pain. In another preferred embodiment, the compounds of the invention are useful for chronic migraine prophylaxis.

Other conditions and disorders include, but are not limited to, autism, childhood learning disorders, depressions, anxieties, sleep disorders, Compounds of the invention may also be useful for the treatment of neurotoxic injury that follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest.

The term "treating" when used in connection with the foregoing disorders means amelioration, prevention or relief from the symptoms and/or effects associated with these disorders and includes the prophylactic administration of a compound of the invention, a mixture thereof, or a pharmaceutically acceptable salt of either, to substantially diminish the likelihood or seriousness of the condition.

B. Models of Disease

In animals, several established models of learning and memory are available to examine the beneficial cognitive enhancing effects and potential related side effects of treatment. Descriptions of tests that may be employed to assess changes in cognition in non-human species are given in the following references and references cited therein. Each of the following references is incorporated by reference into this application in their entirety: Sarter, M., Intern. *J. Neuroscience*, 1987, 32:765-774; *Methods and Findings in Experimental and Clinical Pharmacology* 1998, 20(3), 249-277; *Indian Journal of Pharmacology* 1997, 29(4), 208-221. The tests include the Morris water maze (Stewart and Morris, In "*Behavioral Neuroscience. A Practical Approach*. Volume I", 1993, R. Saghal, Ed., 107-122; Morris, R. *Journal of neuroscience methods* 1984, 11(1), 47-60), delayed non-match to sample (Bontempi, B, et al, *Journal of Pharmacology and Experimental Therapeutics* 2001, 299(1), 297-306.; Alvarez, P; Zola-Morgan, S; Squire, L. R. *Proc Natl Acad Sci U. S. A.* 1994 7;91(12), 5637-41.), delayed Alternation (also called delayed non-matching to position; Roux, S; Hubert, I; Lenegre, A; Milinkevitch, D; Porsolt, R D. *Pharmacol Biochem Behav.* 1994 49(3), 83-8; Ohta, H; Ni, X. H.; Matsumoto, K; Watanabe, H, *Jpn J Pharmacol.* 1991, 56(3), 303-9), social discrimination models (Engelmann, M; Wotjak, C. T.; Landgraf R. *Physiol Behav.* 1995, 58(2), 315-21), social recognition test (also called delay-induced forgetting; Lemaire, M; Bohme, G. A.; Piot. O; Roques, B. P.; Blanchard, J. C. *Psychopharmacology (Berl).* 1994,115(4):435-40), contextual fear conditioning (Barad, M; Bourtchouladze, R; Winder, D G; Golan, H; Kandel, E. *Proc Natl Acad Sci U S A.* 1998, 95(25), 15020-5; Bourtchouladze, R.; Frenguelli, B.; Blendy, J.; Cioffi, D.; Schutz, G.; Silva, A. J. *Cell,* 1994, 79, 59-68), novel object recognition (Ennaceur, A.; Delacour, J. *Behav. Brain Res.* 1988, 31, 47-59; Ennaceur, A.; Cavoy, A.; Costa, J. C.; Delacour, J. *Behav. Brain Res.,* 1989, 33, 197-207), and conditioned fear extinction (Walker, D L; Ressler, K J; Lu, K. T., Davis, M., *J Neurosci.* 2002, 22(6), 2343-51; Davis, M.; Ressler, K.; Rothbaum, B. O.; Richardson, R. *Biol. Psychiatry,* 2006, 60, 369-375).

The Morris water maze is one of the best-validated models of learning and memory, and it is sensitive to the cognitive enhancing effects of a variety of pharmacological agents. The task performed in the maze is particularly sensitive to manipulations of the hippocampus in the brain, an area of the brain important for spatial learning in animals and memory consolidation in humans. Moreover, improvement in Morris water maze performance is predictive of clinical efficacy of a compound as a cognitive enhancer. For example, treatment with cholinesterase inhibitors or selective muscarinic cholinergic agonists reverse learning deficits in the Morris maze animal model of learning and memory, as well as in clinical populations with dementia. In addition, this animal paradigm accurately models the increasing degree of impairment with advancing age and the increased vulnerability of the memory trace to pre-test delay or interference which is characteristic of amnesiac patients.

Contextual fear conditioning is a form of associative learning in which animals learn to fear a new environment (or an emotionally neutral conditioned stimulus) because of its temporal association with an aversive unconditioned stimulus (US), such as a foot shock. When exposed to the same context or conditioned stimulus at a later time, conditioned animals show a variety of conditioned fear responses, including freezing behavior. Because robust learning can be triggered with a single training trial, contextual fear conditioning has been used to study temporally distinct processes of short-term and long-term memory. Contextual fear conditioning is believed to be dependent on both the hippocampus and amygdala function.

Another example of learning is called fear extinction, a process exhibited in both human and animals, including rodents. Extinction of fear refers to the reduction in the measured level of fear to a cue previously paired with an aversive event when that cue is presented repeatedly in the absence of the aversive event. Extinction of fear is not the erasure of the original fear memory, but instead results from a new form of learning that acts to inhibit or suppress the original fear memory (Bouton, M. D.; Bolles, R. C. *J. Exp. Psychol. Anim. Behav. Process.* 1979, 5, 368-378; Konorski, J. *Inegrative Activity of the Brain: An Interdiscipinary Approach,* 1967, Chicago: The University of Chicago Press; Pavlov, I. P. *Conditioned Reflexes.* 1927, Oxford, United Kingdom: Oxford University Press.). The literature also suggests that glutamate acting at the N-methyl D-aspartate (NMDA) receptor is critically involved in learning and memory (Bear, M. F. *Proc. Nat. Acad. Sci.* 1996, 93, 13453-13459; Castellano, C.; Cestari, V.; Ciamei, A. *Curr. Drug Targets,* 2001, 2, 273-283; Morris, R. G.; Davis, S.; Butcher, S. P. *Philos. Trans. R Soc. Lond. B Biol. Sci.* 1990. 329, 187-204; Newcomer, J. W.; Krystal, J. H. *Hippocampus,* 2001, 11, 529-542.). There is also evidence that the NMDA receptor is involved with extinction of fear. For example, NMDA antagonists such as 2-amino-5-phosphopentanoic acid (APV) are known to block fear extinction (Davis, M.; Ressler, K.; Rothbaum, B. O.; Richardson, R. *Biol. Psychiatry,* 2006, 60, 369-375; Kehoe, E. J.; Macrae, M.; Hutchinson, C. L. *Psychobiol.* 1996, 24, 127-135; Lee, H.; Kim, J. J. *J. Neurosci.* 1998, 18, 8444-8454; Szapiro, G.; Vianna, M. R.; McGaugh, J. L.; Medina, J. H.; Izquierdo, I. *Hippocampus,* 2003, 13, 53-58.), and NMDA agonists (such as the partial agonist D-cycloserine), are known to facilitate fear extinction (Davis, M.; Ressler, K.; Rothbaum, B. O.; Richardson, R. *Biol. Psychiatry,* 2006, 60, 369-375; Ledgerwood, L.; Richardson, R.; Cranney, *J. Behav. Neurosci.* 2003, 117 341-349; Walker, D. L.; Ressler, K. J.; Lu K.-T.; Davis, M. *J. Neurosci.* 2002, 22, 2343-235 1). Additional experimental conditions for fear extinction tests may be found in the references cited in this paragraph, and are incorporated by reference.

In human exposure therapy, a patient is repeatedly exposed for prolonged periods to a feared object or situation in the absence of aversive consequences. As a result, the patient is often able to face their feared cues or situations with less fear and avoidance (extinction retention) due to the learning that took place during exposure therapy (extinction training). It has been shown that agents, such as D-cycloserine, that improve extinction in animals also improve the effectiveness of exposure-based psychotherapy. Examples of exposure based cognitive-behavioral therapy (CBT) improved by agents that improve extinction include exposure to phobic objects as therapy for phobia disorders (For acrophobia, see Davis, M.; Ressler, K.; Rothbaum, B. O.; Richardson, R. *Biol. Psychiatry,* 2006, 60, 369-375; Ressler, K. J.; Rothbaum, B. O.; Tannenbaum, L.; Anderson, P.; Graap, K.; Zimand, E.; Hodges, L.; Davis, M. *Archives Gen. Psychiatry* 2004, 61, 1136-1144.), exposure to phobic situations as therapy for panic disorders (For social anxiety disorder, see Hoffmann, S. G.; Meuret, A. E.; Smits, J. A.; Simon, N. M.; Pollack, M. H.; Eisenmenger, K.; Shiekh, M.; Otto, M. W. *Arch. Gen. Psychiatry* 2006, 63, 298-304; Hofmann, S. G.; Pollack, M. H.; Otto, M. W. *CNS Drug Reviews* 2006, 12, 208-217), recollection of traumatic memories as therapy for Post-Traumatic Stress Disorder, exposure to cues associated with drug cravings as therapy for drug addiction, and exposure to cues associated with smoking as therapy for smoking cessation. Because of the cognitive, learning aspects associated with psychotherapy based treatment for disorders such as phobias, anxiety, Post-Traumatic Stress Disorder, and Addiction, compounds of the invention are useful as an adjunct with psychotherapy for the treatment of these conditions. Clinically, compounds of the invention are useful as an adjunct to shorten the number of therapy sessions required or improve the therapeutic outcome of therapy.

In humans, methods for improving learning and memory may be measured by such tests as the Wechsler Memory Scale and the Minimental test. A standard clinical test for determining if a patient has impaired learning and memory is the Minimental Test for Learning and Memory (Folstein et al., J. Psychiatric Res. 12:185, 1975), especially for those suffering from head trauma, Korsakoffs disease or stroke. The test result serves as an index of short-term, working memory of the kind that deteriorates rapidly in the early stages of dementing or amnesiac disorders. Ten pairs of unrelated words (e.g., army-table) are read to the subject. Subjects are then asked to recall the second word when given the first word of each pair. The measure of memory impairment is a reduced number of paired-associate words recalled relative to a matched control group. Improvement in learning and memory constitutes either (a) a statistically significant difference between the performance of treated patients as compared to members of a placebo group; or (b) a statistically significant change in performance in the direction of normality on measures pertinent to the disease model. Animal models or clinical instances of disease exhibit symptoms which are by definition distinguishable from normal controls. Thus, the measure of effective pharmacotherapy will be a significant, but not necessarily complete, reversal of symptoms. Improvement can be facilitated in both animal and human models of memory pathology by clinically effective "cognitive enhancing" drugs which serve to improve performance of a memory task. For example, cognitive enhancers which function as cholinomimetic replacement therapies in patients suffering from dementia and memory loss of the Alzheimer's type significantly improve short-term working memory in such paradigms as the paired-associate task. Another potential application for therapeutic interventions against memory impairment is suggested by age-related deficits in performance which are effectively modeled by the longitudinal study of recent memory in aging mice.

The Wechsler Memory Scale is a widely used pencil-and-paper test of cognitive function and memory capacity. In the normal population, the standardized test yields a mean of 100 and a standard deviation of 15, so that a mild amnesia can be detected with a 10-15 point reduction in the score, a more severe amnesia with a 20-30 point reduction, and so forth. During the clinical interview, a battery of tests, including, but not limited to, the Minimental test, the Wechsler memory scale, or paired-associate learning are applied to diagnose symptomatic memory loss. These tests provide general sensitivity to both general cognitive impairment and specific loss of learning/memory capacity (Squire, 1987). Apart from the specific diagnosis of dementia or amnestic disorders, these clinical instruments also identify age-related cognitive decline which reflects an objective diminution in mental function consequent to the aging process that is within normal limits given the person's age (Diagnostic and Statistical Manual of Mental Disorders, 4$^{th}$ Edition, DSM IV, American Psychiatric Association, 1994). As noted above, "improvement" in learning and memory within the context of the present invention occurs when there is a statistically significant difference in the direction of normality in the paired-associate test, for example, between the performance of therapeutic agent treated patients as compared to members of the placebo group or between subsequent tests given to the same patient.

In animals, many established models of schizophrenia are available to examine the beneficial effects of treatment; many of which are described in the following references, as well as references cited within, and are incorporated by reference: Saibo *Kogaku* 2007, 26(1), 22-27; Cartmell, J.; Monn, J. A.; Schoepp, D. D. *J. Pharm. Exp. Ther.* 1999, 291(1), 161-170; Rowley, M; Bristow, L. J.; Hutson, P. H. *J. Med. Chem.* 2001 15;44(4), 477-501; Geyer, M. A.; Ellenbroek, B; *Prog Neuropsychopharmacol Biol Psychiatry* 2003, 27(7):1071-9; Geyer, M. A.; Krebs-Thomson, K; Braff, D. L.; Swerdlow, N. R. *Psychopharmacology (Berl).* 2001 156(2-3):117-54; Jentsch, J. D.; Roth, R. H. *Neuropsychopharmacology* 1999, 20(3):201-25. The tests include Prepulse Inhibition (Dulawa, S. C.; Geyer, M. A. *Chin J Physiol*. 1996, 39(3):139-46), PCP stereotypy test (Meltzer et al (In "PCP (Phencyclidine): Historical and Current Perspectives", ed. E. F. Domino, NPP Books, Ann Arbor, 1981, 207-242), Amphetamine stereotypy test (Simon and Chermat, *J. Pharmacol. (Paris)*, 1972, 3, 235-238), PCP hyperactivity (Gleason, S. D.; Shannon, H. E. *Psychopharmacology (Berl)*. 1997, 129(1):79-84) and MK-801 hyperactivity (Corbett, R; Camacho, F; Woods, A. T.; Kerman, L. L.; Fishkin, R. J.; Brooks, K; Dunn, R. W. *Psychopharmacology (Berl)*. 1995, 120(1):67-74.

The prepulse inhibition test may be used to identify compounds that are effective in treating schizophrenia. The test is based upon the observations that animals or humans that are exposed to a loud sound will display a startle reflex and that animals or humans exposed to a series of lower intensity sounds prior to the higher intensity test sound will no longer display as intense of a startle reflex. This is termed prepulse inhibition. Patients diagnosed with schizophrenia display defects in prepulse inhibition, that is, the lower intensity prepulses no longer inhibit the startle reflex to the intense test sound. Similar defects in prepulse inhibition can be induced in animals via drug treatments (scopolamine, ketamine, PCP or MK-801) or by rearing offspring in isolation. These defects in prepulse inhibition in animals can be partially reversed by drugs known to be efficacious in schizophrenia patients. It is felt that animal prepulse inhibition models have face value for predicting efficacy of compounds in treating schizophrenia patients.

In animals, many established models of pain are available to examine the beneficial effects of treatment; many of which are reviewed in Methods in Pain Research, CRC Press, 2001, Kruger, L. (Editor). Tests of acute pain include the tail flick (d'Amour and Smith, *J. Pharmacol. Exp. Ther.* 1941, 72, 74-79), hot plate (Eddy, N. B.; Leimbach, D. *J Pharmacol Exp Ther.* 1953, 107(3):385-93), and paw withdrawal tests. The phenylbenzoquinone writhing assay is a measure of peritoneovisceral or visceral pain. Persistent pain tests, which use an irritant or foreign chemical agent as the nociceptive stimulus, include the formalin test (Wheeler-Aceto, H; Cowan, A *Psychopharmacology (Berl)*. 1991, 104(1):35-44), Freund's adjuvant (Basile, A. S. et al *Journal of Pharmacology and Experimental Therapeutics* 2007, 321(3), 1208-1225; Ackerman, N. R. et al ; *Arthritis & Rheumatism* 1979, 22(12), 1365-74), capsaicin (Barrett, A. C. et al *Journal of Pharmacology and Experimental Therapeutics* 2003, 307(1), 237-245), and carrageenin models. These models have an initial, acute phase, followed by a second, inflammatory phase.

Neuropathic pain models are reviewed in Wang and Wang, Advanced Drug Delivery Reviews 2003, and include the Spinal Nerve Ligation (SNL) model (also called the Chung Model; Kim, S. H.; Chung, J. M. *Pain* 1992 50(3):355-63; Chaplan et al., *Journal of Neuroscience Methods* 1994, 53(1): 55-63; Chaplan S R, Bach F W, Pogrel J W,.), Chronic Constriction Injury (CCI) model (also called the Bennett Model; Bennett, G. J; Xie, Y. K *Pain* 1988 33(1):87-107.), Progressive Tactile Hypersensitivity (PTH) model (Decosterd, I. *Pain*, 2002, 100(1), 155-162; *Anesth. Analg.* 2004, 99, 457-463), Spared Nerve Injury (SNI) model (Decosterd, I. *Pain,* 2002, 100(1), 155-162; *Anesth. Analg.* 2004, 99, 457-463), the lumbar nerve ligation model (Ringkamp, M; Eschenfelder, S; Grethel, E. J.; Häbler, H. J., Meyer, R. A., Jänig, W., Raja, S. N. *Pain*, 1999, 79(2-3), 143-153), and streptozocin— or chemotherapy induced diabetic neuropathy (Courteix, C.; Eschalier, A.; Lavarenne, J. *Pain,* 1993, 53(1), 81-88; Aubel, B. et al *Pain* 2004, 110(1-2), 22-32.).

Opioids, such as morphine, display robust efficacy in models of acute pain, such as the tail flick and hot plate tests, as well as in both the initial, acute phase and the second, inflammatory phase of persistent pain tests, such as the formalin test. Opioids also display efficacy in neuropathic pain models, such as the Spinal Nerve Ligation (SNL) model. The general analgesic effects of opiate compounds such as morphine in neuropathic pain models, however, are suggested by the increase in paw withdrawal threshold (PWT) in both the injured and the contralateral (uninjured) paw. Compounds that are useful specifically for the treatment of persistent or chronic pain states (e.g., neuropathic pain), such as gabapentin, tend to display efficacy in models of persistent inflammatory and neuropathic pain, such as the formalin (second phase) and SNL models. Compounds of this type, however, tend to increase PWT in the SNL model in only the injured paw. In addition, these compounds fail to display efficacy in acute tests such as the tail flick test and the hot plate test, and also fail to display efficacy in the initial, acute phase of the formalin test. The lack of effect of compounds in the acute pain tests supports the notion that the antinociceptive action of these compounds is related to specific mechanisms associated with a central sensitized state following injury. As a result, compounds that are efficacious in neuropathic pain model(s), such as the SNL (Chung) model, and the second phase of the formalin test, but are not efficacious in acute pain models, such as hot plate and tail flick, or in the first phase of the formalin test suggest that these compounds are more likely to be effective in persistent and chronic, rather than acute, pain states (see Table 1). In addition, their ability to increase PWT in the SNL model should be specific for the ipsilateral (injured) paw. Relevant references follow, and are included by reference. Singh, L. et al, *Psychopharmacology,* 1996, 127, 1-9. Field, M. J. et al *Br. J. Pharmacol.* 1997, 121, 1513-1522. Iyengar, S. et al, *J. Pharmacology and Experimental Therapeutics,* 2004, 311, 576-584. Shimoyama, N. et al *Neuroscience Letters,* 1997, 222, 65-67. Laughlin, T. M. et al *J. Pharmacology and Experimental therapeutics,* 2002, 302, 1168-1175. Hunter, J. C. et al *European J. Pharmacol.* 1997, 324, 153-160. Jones, C. K. et al *J. Pharmacology and Experimental therapeutics,* 2005, 312, 726-732. Malmberg, A. B.; Yaksh, T. L. *Anesthesiology,* 1993, 79, 270-281. Bannon, A W et al *Brain Res.,* 1998, 801, 158-63.

In a preferred embodiment, the compounds of the invention are useful for the treatment of persistent or chronic pain states (e.g., neuropathic pain). As described above, such compounds may be profiled in vivo by evaluating their efficacy in models of both acute and neuropathic pain. Preferred compounds demonstrate efficacy in neuropathic pain models, but not in acute pain models.

TABLE 1

Profile of morphine and gabapentin in a variety of animal models

| Animal Model | Morphine | Gabapentin |
|---|---|---|
| Acute Pain | | |
| Hot plate | + | − |
| Tail flick | + | − |
| Formalin (early phase) | + | − |
| Tissue Injury/Inflammatory Pain | | |
| Formalin (second phase) | + | + |
| Carrageenan | + | + |
| Nerve Injury/Neuropathic Pain | | |
| Spinal Nerve Ligation (SNL; Chung) | + | + |
| Chronic Constriction Injury (CCI; Bennet) | + | + |

There are various animal models with chronic brain dysfunctions thought to reflect the processes underlying human epilepsy and seizures/convulsions, such as those described in *Epilepsy Res. June* 2002;50(1-2):105-23. Such chronic models include the kindling model of temporal lobe epilepsy (TLE), post-status models of TLE in which epilepsy develops after a sustained status epilepticus, and genetic models of different types of epilepsy. Currently, the kindling model and post-status models, such as the pilocarpine or kainate models, are the most widely used models for studies on epileptogenic processes and on drug targets by which epilepsy can be prevented or modified. Furthermore, the seizures in these models can be used for testing of antiepileptic drug effects. A comparison of the pharmacology of chronic models with models of acute (reactive or provoked) seizures in previously healthy (non-epileptic) animals, such as the maximal electroshock seizure test, demonstrates that drug testing in chronic models of epilepsy yields data which are more predictive of clinical efficacy and adverse effects.

The following examples are provided to illustrate selected embodiments of the invention and are not to be construed as limiting its scope.

EXAMPLES

General Procedures

General Procedure 1: Synthesis of Fused Pyrrole Analogs

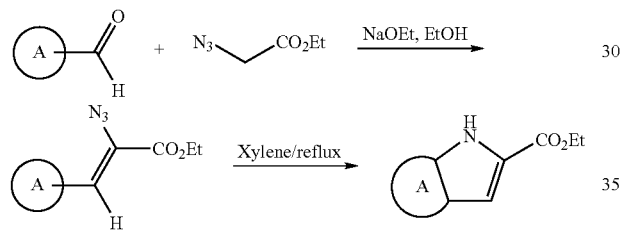

In the above Scheme, ring A represents any substituted or unsubstituted 5-membered, aromatic ring. Exemplary aromatic rings include furans.

A) Condensation of an Aldehyde with Ethyl Azidoacetate

A solution of the aldehyde (e.g., 1.61 g, 8.41 mmol) and about 4 to about 7 equivalents of ethyl azidoacetate (e.g., 4.34 g, 33.7 mmol) in anhydrous EtOH (e.g., 10.5 mL) was added dropwise to a solution of sodium (e.g., 0.8 g) in anhydrous EtOH (e.g., 50.0 mL) at a temperature between about 0° C. and about −45° C. (typically between about −10 and about −5° C. (e.g., NaCl/ice)). The reaction mixture was stirred for about 1 hour (h) while the temperature was maintained below 0° C. and was then allowed to warm to ambient temperature (e.g., overnight). The mixture was quenched with a cold solution of saturated aqueous $NH_4Cl$ or was diluted with water (e.g., 0.5 L). The product was extracted with diethyl ether or ethyl acetate (EtOAc) (e.g., 3×0.2 L) and the combined organic phases were washed with saturated aqueous NaCl solution (2×0.1 L), dried (e.g., over $Na_2SO_4$) and filtered. The solvent was removed in vacuo to give the ethyl azidoacrylate. Alternatively, the solvent was reduced in vacuo (e.g., to about 50 mL) and the resulting solution was used in the next reaction step.

B) Cyclization of the Ethyl Azidoacrylate

A solution of the above ethyl azidoacrylate in o- or m-xylene (e.g., 150 mL) was heated to reflux for a time period between about 15 minutes (min) and 14 h (typically about 1 h). The reaction mixture was then allowed to cool to ambient temperature. The solution was concentrated in vacuo and the crude product was purified (e.g., silica gel column chromatography) to give the fused pyrrole ethyl ester.

General Procedure 2: Saponification of Ethyl and Methyl-Esters

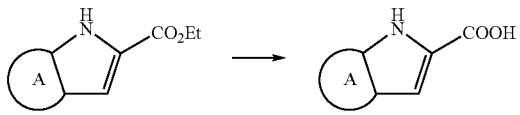

To a solution or suspension of the ester (e.g., 0.33 g, 1.2 mmol) in MeOH or EtOH (e.g., 16.5 mL) was added an aqueous base, such as 10M NaOH (e.g., 0.6 mL, 6 mmol), 5M KOH (e.g., 1.2 mL, 6 mmol) or 1M LiOH (e.g., 6 mL). The solution was heated to a temperature between about 80° C. and refluxed for a time period between about 30 min and about 20 h (e.g., 5 h). The reaction mixture was cooled to rt and was then acidified. In one example, the mixture was poured into water (e.g., 200 mL) and the pH of the resulting mixture was adjusted to about pH 1-2 with HCl. In another example, excess solvent was removed in vacuo and the residue was dissolved in 5% citric acid (e.g., 15 mL). In yet another example, the solvent was removed in vacuo and the residue was dissolved in a saturated solution of $NH_4Cl$ (e.g., 15 mL). The acidified solution was then extracted (e.g., 3×100 mL EtOAc) and the combined organic layers were washed (e.g., with brine), dried (e.g., over $Na_2SO_4$), filtered and concentrated in vacuo to give the carboxylic acid.

Example 1

Synthesis of Fused Furan Pyrrole Analogs 1.1. Synthesis of Intermediate Aldehydes 1.1.a) Synthesis of 4-phenethyl-furan-2-carbaldehyde A solid mixture of 4-bromo-2-furaldehyde (1.50 g, 8.57 mmol), $PdCl_2(PhCN)_2$ (197 mg, 0.514 mmol) and CuI (65.0 mg, 0.343 mmol) was flushed under an argon stream for 1 minute (min). A solution of $HP(t-butyl)_3BF_4$ (298 mg, 1.03 mmol) and diisopropylamine (1.80 mL, 12.9 mmol) in dioxane (9 mL) was added to the solid mixture followed by phenylacetylene (1.13 mL, 10.3 mmol). The reaction was allowed to stir at room temperature (rt) under an atmosphere of argon for 15 hours (h) before being filtered through a plug of silica gel with ethyl acetate (EtOAc). The solution was then concentrated in vacuo and chromatographed over silica gel to give 4-phenylethynyl-furan-2-carbaldehyde as a colorless oil (1.54 g, 92%). $R_f$=0.35 (1:9 heptane/EtOAc); $^1$H NMR (400 MHz, $CDCl_3$) δ ppm 9.68 (d, J=0.5 Hz, 1 H) 7.90 (s, 1 H) 7.48-7.55 (m, 2 H) 7.35-7.40 (m, 3 H) 7.33 (d, J=0.7 Hz, 1 H).

To a solution of 4-phenylethynyl-furan-2-carbaldehyde (1.54 g, 7.84 mmol) in MeOH was added palladium on carbon (Pd/C) (154 mg, 10% Pd by weight). A vacuum was applied to the reaction mixture and back filled with $H_2$ 4 times. The reaction was then allowed to stir at rt for 14 h under an atmosphere of $H_2$ before being filtered through a plug of Celite® with EtOAc. The reaction was then concentrated in vacuo to give 4-phenethyl-furan-2-carbaldehyde as a colorless oil (1.53 g, 97%). $^1$H NMR (400 MHz, $CDCl_3$) δ ppm 9.59 (d, J=0.6 Hz, 1 H) 7.40 (d, J=0.8 Hz, 1 H) 7.28-7.34 (m, 2 H) 7.20-7.26 (m, 1 H) 7.14-7.20 (m, 2 H) 7.05 (d, J=0.6 Hz, 1 H) 2.87-2.94 (m, 2 H) 2.78-2.85 (m, 2 H).

1.1.b) Synthesis of 5-benzyl-furan-2-carbaldehyde

A solution of Pd(OAc)$_2$ (64 mg, 0.29 mmol), triphenylphosphine (TPP) (0.30 g, 1.1 mmol) and isopropanol (3.6 mL) in acetonitrile (7.4 mL) was added to a solid mixture of 2-boronic acid-5-furaldehyde (0.80 g, 5.7 mmol), diethylbenzylphosphonate (1.5 g, 6.3 mmol) and K$_3$PO$_4$ (1.8 g, 8.6 mmol). The reaction mixture was flushed with a stream of nitrogen and heated to 80° C. overnight. The mixture was then cooled to room temperature and filtered through a plug of silica gel with ethyl acetate. The organic solution was then concentrated in vacuo and the resultant solid was chromatographed over silica gel to give 5-benzyl-furan-2-carbaldehyde as a brown solid (0.37 g, 65%). $^1$H NMR (400 MHz, CDCl$_3$) δ ppm 9.56 (s, 1 H) 7.29-7.38 (m, 3 H) 7.24-7.28 (m, 2 H) 7.17 (d, J=3.5 Hz, 1 H) 6.19 (d, J=3.6 Hz, 1 H) 4.07 (s, 2 H).

1.1.c) Synthesis of 4-benzyl-furan-2-carbaldehyde

The title compound was synthesized from 5-formylfuran-3-boronic acid pinacol ester (878 mg, 3.95 mmol), and benzyl diethyl phosphate (1.25 g, 5.14 mmol) using the same conditions used to synthesize 5-benzyl-furan-2-carbaldehyde, with the exception that TPP and Pd(OAc)$_2$ were dissolved in 2:1 CH$_3$CN/isopropyl alcohol. Purification by flash chromatography yielded 4-benzyl-furan-2-carbaldehyde as a white solid (300 mg, 41%). $^1$H NMR (400 MHz, CDCl$_3$) δ ppm 9.56 (s, 1 H) 7.29-7.38 (m, 3 H) 7.24-7.28 (m, 2 H) 7.17 (d, J=3.5 Hz, 1 H) 6.19 (d, J=3.6 Hz, 1 H) 4.07 (s, 2 H).

1.1.d) Synthesis of 4-vinylfuran-2-carbaldehyde

The title compound was synthesized from 4-bromo-furan-2-carbaldehyde (1.1 g, 6.29 mmol) and vinylboronic acid dibutyl ester (1.67 mL, 7.54 mmol) using the same conditions used to synthesize 5-benzyl-furan-2-carbaldehyde, with the exception that the reaction was run in N,N-dimethylformamide (DMF) (20 mL). Purification by flash chromatography (0-30% EtOAc in heptane) provided 4-vinylfuran-2-carbaldehyde as an orange oil; Yield 282 mg (37%). $^1$H NMR (400 MHz, CDCl$_3$) δ ppm 5.31 (dd, J=10.88, 0.93 Hz, 1 H), 5.61 (dd, J=17.57, 0.54 Hz, 1 H), 6.56 (dd, J=17.55, 10.91 Hz, 1 H), 7.37 (s, 1 H), 7.67 (s, 1 H), 9.66 (d, J=0.59 Hz, 1 H).

1.1.e) Synthesis of (Z)-4-(prop-1-enyl)furan-2-carbaldehyde

The title compound was synthesized from 4-bromo-furan-2-carboxaldehyde (1.1 g, 6.3 mmol, 1 equiv) and cis-propene boronic acid (0.65 g, 7.5 mmol, 1.2 equiv) using the conditions to synthesize 5-benzyl-furan-2-carbaldehyde, with the exception that the reaction was run in DMF (20 mL). The resulting residue was purified via ISCO Companion (0-25% EtOAc/heptane over 30 min, retention time of product: 23-26 min) to give (Z)-4-(prop-1-enyl)furan-2-carbaldehyde (0.4130 g, 48% yield). LC/MS m/e 136.8 (M+H). $^1$H NMR (400 MHz, CD$_3$CN) δ (ppm): 9.59 (d, J=0.63 Hz, 1 H), 7.83 (s, 1 H), 7.42 (s, 1 H), 6.23 (dd, J=11.40, 1.68 Hz, 1 H), 5.79-5.89 (m, 1 H), 1.87 (dd, J=7.10, 1.78 Hz, 3 H).

1.1.f) Synthesis of (E)-4-styrylfuran-2-carbaldehyde

The title compound was synthesized from 4-bromo-furan-2-carboxaldehyde (1.1 g, 6.3 mmol, 1 equiv) and trans-phenylvinyl-boronic acid (1.4 g, 9.4 mmol, 1.5 equiv) using the conditions used to synthesize 5-benzyl-furan-2-carbaldehyde, with the exception that the reaction was run in DMF (25 mL). The resulting residue was purified via ISCO Companion (0-30% EtOAc/heptane) and preparative HPLC using the Chromeleon purification system (0.1% formic acid/1% acetonitrile mixture in water (aqueous phase) and methanol (no modifier added—organic phase) using a 50 mm Dynamax HPLC C-18 column at 28 mL/min (initial gradient of 40% methanol and increasing to 100% over 7 min)) afforded a clean product, retention time of product: 3.4-3.6 min. Amount of (E)-4-styrylfuran-2-carbaldehyde isolated: 89.1 mg (7% yield). $^1$H NMR (400 MHz, CD$_3$CN) δ (ppm): 9.62 (d, J=0.59 Hz, 1 H), 7.91 (s, 1 H), 7.63 (d, J=0.63 Hz, 1 H), 7.50-7.55 (m, 2 H), 7.35-7.42 (m, 2 H), 7.26-7.32 (m, 1 H), 7.08 (s, 2 H).

1.2. Synthesis of Intermediate Esters

The following ethyl esters were synthesized from the indicated aldehyde according to General Procedure 1A (to yield an intermediate acrylate) followed by General Procedure 1B.

1.2.a) Synthesis of ethyl 4H-furo[3,2-b]pyrrole-5-carboxylate

The title compound was synthesized from 2-furaldehyde (1.44 g, 15.0 mmol) and was purified by silica gel column chromatography (0 to 25% EtOAc in heptane over 25 min) to give ethyl 4H-furo[3,2-b]pyrrole-5-carboxylate as a pink solid (0.330 g, 12%). $R_f$=0.42 (50:50 heptane/EtOAc); $^1$H NMR (400 MHz, CDCl$_3$) δ (ppm) 8.63 (s, 1 H) 7.53 (s, 1 H) 6.81 (s, 1 H) 6.47 (s, 1 H) 4.36 (q, J=7.1 Hz, 2 H) 1.38 (t, J=7.1 Hz, 3 H).

1.2.b) Synthesis of ethyl 3-phenethyl-4H-furo[3,2-b]pyrrole-5-carboxylate

A) 2-Azido-3-(4-phenethyl-furan-2-yl)-acrylic acid ethyl ester was synthesized from 4-phenethyl-furan-2-carbaldehyde (1.53 g, 7.64 mmol) to give a colorless oil (0.718 g, 30%) after purification by silica gel column chromatography. $^1$H NMR (400 MHz, CDCl$_3$) δ ppm 7.28-7.34 (m, 2 H) 7.17-7.25 (m, 4 H) 6.99 (s, 1 H) 6.81 (s, 1 H) 4.35 (q, J=7.1 Hz, 2 H) 2.86-2.94 (m, 2 H) 2.73-2.80 (m, 2 H) 1.38 (t, J=7.1 Hz, 3 H).

B) The title compound was prepared from 2-azido-3-(4-phenethyl-furan-2-yl)-acrylic acid ethyl ester and was purified by silica gel column chromatography to give ethyl 3-phenethyl-4H-furo[3,2-b]pyrrole-5-carboxylate as a white solid (613 mg, 94%). $^1$H NMR (400 MHz, CDCl$_3$) δ ppm 7.48 (br s., 1 H) 7.28-7.39 (m, 4 H) 7.23-7.26 (m, 2 H) 6.67 (d, J=1.8 Hz, 1 H) 4.30 (q, J=7.1 Hz, 2 H) 2.90-2.99 (m, 4 H) 1.36 (t, J=7.2 Hz, 3 H).

1.2.c) Synthesis of ethyl 2-benzyl-4H-furo[3,2-b]pyrrole-5-carboxylate

A) 2-Azido-3-(5-benzyl-furan-2-yl)-acrylic acid ethyl ester was prepared from 5-benzyl-furan-2-carbaldehyde (295 mg, 1.58 mmol) and was purified by silica gel column chromatography to give a brown oil (35.0 mg, 7%). $^1$H NMR (400 MHz, CDCl$_3$) δ ppm 7.30-7.36 (m, 3 H) 7.24 (d, J=0.6 Hz, 2 H) 7.09 (dd, J=3.4, 0.4 Hz, 1 H) 6.21-6.24 (m, 1 H) 6.05-6.08 (m, 1 H) 4.35 (q, J=7.1 Hz, 2 H) 4.05 (s, 2 H) 1.35-1.39 (m, 3 H).

B) The title compound was prepared from 2-azido-3-(5-benzyl-furan-2-yl)-acrylic acid ethyl ester and was purified by silica gel column chromatography to afford ethyl 2-benzyl-4H-furo[3,2-b]pyrrole-5-carboxylate as a tan solid (17 mg, 53%). $^1$H NMR (400 MHz, CDCl$_3$) δ ppm 8.61 (br. s., 1

H) 7.31-7.37 (m, 2 H) 7.23-7.31 (m, 3 H) 6.74 (dd, J=1.6, 0.9 Hz, 1 H) 6.10 (d, J=0.9 Hz, 1 H) 4.34 (q, J=7.1 Hz, 2 H) 4.07 (s, 2 H) 1.37 (t, J=7.1 Hz, 3 H).

1.2.d) Synthesis of ethyl 3-benzyl-4H-furo[3,2-b]pyrrole-5-carboxylate

A) 2-Azido-3-(4-benzyl-furan-2-yl)-acrylic acid ethyl ester was synthesized from 4-benzyl-furan-2-carbaldehyde (0.300 g, 1.61 mmol) and purified to give a pale yellow oil (135 mg, 28%). $^1$H NMR (400 MHz, CD$_3$CN) δ ppm 7.42 (d, J=0.9 Hz, 1 H) 7.30 (d, J=7.1 Hz, 2 H) 7.19-7.28 (m, 3 H) 7.00 (s, 1 H) 6.75 (s, 1 H) 4.29 (q, J=7.1 Hz, 2 H) 3.79 (s, 2 H) 1.32 (t, J=7.1 Hz, 3 H).

B) The title compound was prepared from 2-azido-3-(4-benzyl-furan-2-yl)-acrylic acid ethyl ester and was purified by silica gel column chromatography to afford ethyl 3-benzyl-4H-furo[3,2-b]pyrrole-5-carboxylate as a brown solid (52 mg, 43%). $^1$H NMR (400 MHz, CD$_3$CN) δ ppm 9.57 (br. s., 1 H) 7.40 (s, 1 H) 7.28-7.35 (m, 4 H) 7.19-7.27 (m, 1 H) 6.68 (d, J=1.8 Hz, 1 H) 4.26 (q, J=7.1 Hz, 2 H) 3.92 (s, 2 H) 1.27-1.34 (m, 3 H).

1.2.e) Synthesis of ethyl 3-vinyl-4H-furo[3,2-b]pyrrole-5-carboxylate

A) Ethyl 2-azido-3-(4-vinylfuran-2-yl)acrylate (398 mg, 52%) was synthesized from 4-vinylfuran-2-carbaldehyde (0.4 g, 3.28 mmol) and was purified by flash chromatography (Isco CombiFlash, 0-5% EtOAc/heptane). $^1$H NMR (400 MHz, CDCl$_3$) δ ppm 1.39 (t, J=7.13 Hz, 3 H), 4.36 (q, J=7.13 Hz, 2 H), 5.23 (dd, J=10.88, 1.22 Hz, 1 H), 5.58 (dd, J=17.52, 1.17 Hz, 1 H), 6.55 (dd, J=17.57, 10.88 Hz, 1 H), 6.81 (s, 1 H), 7.25 (s, 1 H), 7.46 (s, 1 H); LCMS-MS (ESI+) 205.86 (M-N$_2$).

B) The title compound was synthesized from ethyl 2-azido-3-(4-vinylfuran-2-yl)acrylate and was purified by flash column chromatography (Isco CombiFlash, 0-30% EtOAc/heptane) to afford ethyl 3-vinyl-4H-furo[3,2-b]pyrrole-5-carboxylate as a white solid (215 mg, 62%). $^1$H NMR (400 MHz, CDCl$_3$) δ ppm 1.40 (t, J=7.13 Hz, 3 H), 4.38 (q, J=7.13 Hz, 2 H), 5.35 (d, J=10.93, Hz, 1 H), 5.52 (d, J=17.57 Hz, 1 H), 6.63 (dd, J=17.57, 10.88 Hz, 1 H), 6.80 (d, J=1.66 Hz, 1 H), 7.53 (s, 1 H); LCMS-MS (ESI+) 205.85 (M+H).

1.2.f) Synthesis of (Z)-ethyl 3-(prop-1-enyl)-4H-furo[3,2-b]pyrrole-5-carboxylate A) (Z)-ethyl 2-azido-3-(4-((Z)-prop-1-enyl)furan-2-yl)acrylate (663 mg, 87%) was synthesized from (Z)-4-(prop-1-enyl)furan-2-carbaldehyde (0.4130 g, 3.7 mmol, 1 eq.) and was purified via ISCO Companion (0-20% EtOAc/heptane over 19 min, retention time: 3-6 min). $^1$H NMR (400 MHz, CD$_3$CN) δ (ppm): 7.63 (s, 1 H), 7.21 (s, 1 H), 6.78 (s, 1 H), 6.20 (dd, J=11.37, 1.61 Hz, 1 H), 5.71-5.82 (m, 1 H), 4.31 (q, J=7.13 Hz, 2 H), 1.86 (dd, J=7.13, 1.76 Hz, 3 H), 1.33 (t, J=7.13 Hz, 3 H).

B) The title compound was synthesized from (Z)-ethyl 2-azido-3-(4-((Z)-prop-1-enyl)furan-2-yl)acrylate (0.6633 g) and purified via ISCO Companion (0-30% EtOAc/heptane over 30 min, retention time: 26-29 min) to give (Z)-ethyl 3-(prop-1-enyl)-4H-furo[3,2-b]pyrrole-5-carboxylate (145 mg, 25%). LC/MS m/e 219.8 (M+H). $^1$H NMR (400 MHz, CD$_3$CN) δ (ppm): 9.70 (s, 1 H), 7.65 (s, 1 H), 6.72 (d, J=1.71 Hz, 1 H), 6.30-6.37 (m, 1 H), 5.82-5.94 (m, 1 H), 4.24-4.34 (m, 2 H), 1.88 (dd, J=7.05, 1.78 Hz, 3 H), 1.30-1.36 (m, 3 H).

1.2.g) Synthesis of (E)-ethyl 3-styryl-4H-furo[3,2-b]pyrrole-5-carboxylate

A) (E)-Ethyl 2-azido-3-(4-styrylfuran-2-yl)acrylate (36.1 mg, 26%) was synthesized from (E)-4-styrylfuran-2-carbaldehyde (0.0891 g, 0.5 mmol) and was purified via ISCO Companion (0-50%, EtOAc/heptane, over 35 min, retention time: 3-8 min). $^1$H NMR (400 MHz, CD$_3$CN) δ (ppm): 7.71 (s, 1 H), 7.47-7.54 (m, 3 H), 7.34-7.40 (m, 2 H), 7.24-7.30 (m, 1 H), 6.99-7.10 (m, 2 H), 6.79 (s, 1 H), 4.32 (q, J=7.13 Hz, 2 H), 1.34 (t, J=7.10 Hz, 3 H).

B) The title compound was prepared from (E)-ethyl 2-azido-3-(4-styrylfuran-2-yl)acrylate (36.1 mg) and was purified via preparative HPLC using the Chromeleon purification system (60-100% methanol/0.1% formic acid-1% acetonitrile in water, 50 mm Dynamax C-18 column at 28 mL/min over 7 min, retention time 3.5-3.8 min) to give (E)-ethyl 3-styryl-4H-furo[3,2-b]pyrrole-5-carboxylate (18.1 mg, 55% yield). $^1$H NMR (400 MHz, CD$_3$CN) δ (ppm): 10.07 (s, 1 H), 7.75 (s, 1 H), 7.57-7.62 (m, 2 H), 7.40 (t, J=7.61 Hz, 2 H), 7.26-7.32 (m, 1 H), 7.09-7.22 (m, 2 H), 6.78 (d, J=1.71 Hz, 1 H), 4.33 (q, J=7.13 Hz, 2 H), 1.36 (t, J=7.13 Hz, 3 H).

1.5. Synthesis of Carboxylic Acids from Esters

1.5.a) Synthesis of 4H-Furo[3,2-b]pyrrole-5-carboxylic acid (11)

The title compound was synthesized from ethyl 4H-furo[3,2-b]pyrrole-5-carboxylate (0.33 g, 1.84 mmol) according to General Procedure 2 and was purified by silica gel column chromatography (0 to 100% EtOAc in heptane over 30 min) to give 4H-furo[3,2-b]pyrrole-5-carboxylic acid 11 as a light pink solid (0.200 g, 72%). R$_f$=0.07 (1:1 heptane/EtOAc); $^1$H NMR (400 MHz, (CD$_3$)$_2$SO) δ (ppm) 12.34 (s, 1 H) 11.48 (s, 1 H) 7.75 (s, 1 H) 6.68 (s, 1 H) 6.57 (s, 1 H).

1.5.b) Synthesis of 3-phenethyl-4H-furo[3,2-b]pyrrole-5-carboxylic acid (17)

The title compound was prepared from ethyl 3-phenethyl-4H-furo[3,2-b]pyrrole-5-carboxylate (265 mg, 0.935 mmol) according to General Procedure 2 to give 3-phenethyl-4H-furo[3,2-b]pyrrole-5-carboxylic acid 17 as a tan solid (117 mg, 49%). $^1$H NMR (400 MHz, (CD$_3$)$_2$SO) δ ppm 12.34 (br s., 1 H) 11.68 (s, 1 H) 7.51 (s, 1 H) 7.25-7.32 (m, 4 H) 7.15-7.22 (m, 1 H) 6.63 (d, J=1.7 Hz, 1 H) 2.91-2.99 (m, 2 H) 2.73-2.81 (m, 2 H).

1.5.c) Synthesis of 2-benzyl-4H-furo[3,2-b]pyrrole-5-carboxylic acid (24)

The title compound was prepared from ethyl 2-benzyl-4H-furo[3,2-b]pyrrole-5-carboxylate (17 mg, 63 μmol) according to General Procedure 2 to give 2-benzyl-4H-furo[3,2-b]pyrrole-5-carboxylic acid 24 (13 mg, 87%) as a tan solid. $^1$H NMR (400 MHz, (CD$_3$)$_2$SO) δ ppm 12.17 (br. s., 1 H) 11.36

(s, 1 H) 7.19-7.36 (m, 5 H) 6.59 (dd, J=1.7, 0.9 Hz, 1 H) 6.29 (d, J=0.8 Hz, 1 H) 4.04 (s, 2 H).

1.5.d) Synthesis of 3-benzyl-4H-furo[3,2-b]pyrrole-5-carboxylic acid (26)

The title compound was prepared from ethyl 3-benzyl-4H-furo[3,2-b]pyrrole-5-carboxylate (52 mg, 0.19 mmol) according to General Procedure 2 to give 3-benzyl-4H-furo[3,2-b]pyrrole-5-carboxylic acid 26 as a tan solid (41 mg, 87%). $^1$H NMR (400 MHz, (CD$_3$)$_2$SO) δ ppm 12.32 (br. s., 1 H) 11.60 (s, 1 H) 7.57 (s, 1 H) 7.33-7.38 (m, 2 H) 7.25-7.31 (m, 2 H) 7.15-7.21 (m, 1 H) 6.63 (d, J=1.5 Hz, 1 H) 3.84 (s, 2 H). HPLC 99%. LCMS 242 (M+H).

1.5.e) Synthesis of 3-vinyl-4H-furo[3,2-b]pyrrole-5-carboxylic acid (32)

The title compound was synthesized from ethyl 3-vinyl-4H-furo[3,2-b]pyrrole-5-carboxylate (100 mg, 0.49 mmol) according to General Procedure 2 and was purified by flash chromatography (Isco CombiFlash, 0-40% EtOAc/heptane) to give 3-vinyl-4H-furo[3,2-b]pyrrole-5-carboxylic acid 32 (36 mg, 42%). $^1$H NMR (400 MHz, CD$_3$OD) δ ppm 5.29 (dd, J=11.03, 0.73 Hz, 1 H), 5.81-5.88 (m, 1 H), 6.59-6.68 (m, 1 H), 6.72 (s, 1 H), 7.63 (s, 1 H); LCMS-MS (ESI−) 175.8 (M−H); HPLC (UV=99.2%), (ELSD =100%).

1.5.f) Synthesis of (Z)-3-(prop-1-enyl)-4H-furo[3,2-b]pyrrole-5-carboxylic acid (46)

The title compound was synthesized from (Z)-ethyl 3-(prop-1-enyl)-4H-furo[3,2-b]pyrrole-5-carboxylate (0.1445 g, 68 mmol) according to General Procedure 2 and was purified by preparative HPLC using a Chromeleon purification system (50-100% over 7 min methanol/0.1% formic acid-1% acetonitrile in water, 50 mm Dynamax C-18, 28 mL/min) to give (z)-3-(prop-1-enyl)-4H-furo[3,2-b]pyrrole-5-carboxylic acid 46 (40.4 mg, 32% yield). LC/MS m/e 189.8 (M−H). Purity by HPLC: 99.1% (UV); 100% (ELSD). $^1$H NMR (400 MHz, CD$_3$OD) δ (ppm): 7.64 (s, 1 H), 6.72 (s, 1 H), 6.32-6.38 (m, 1 H), 5.81-5.91 (m, 1 H), 1.91 (dd, J=7.03, 1.76 Hz, 3 H).

1.5.g) Synthesis of (E)-3-Styryl-4H-furo[3,2-b]pyrrole-5-carboxylic acid (48)

The title compound was synthesized from (E)-ethyl 3-styryl-4H-furo[3,2-b]pyrrole-5-carboxylate (0.0181 g, 0.071 mmol) according to General Procedure 2A and was purified via preparative HPLC (Chromeleon purification system, 40-100% over 7 min, methanol/0.1% formic acid-1% acetonitrile in water, 50 mm Dynamax C-18, 28 mL/min, retention time of product: 3.9-4.0 min) to give (E)-3-styryl-4H-furo[3,2-b]pyrrole-5-carboxylic acid 48 (4.9 mg, 30%). LC/MS m/e 251.9 (M−H). Purity by HPLC: 97.9% (UV); 100% (ELSD). $^1$H NMR (400 MHz, CD$_3$OD) δ (ppm): 8.40 (s, 1 H), 7.76 (s, 1 H), 7.58-7.62 (m, 2 H), 7.34-7.39 (m, 2 H), 7.31 (d, J=16.40 Hz, 1 H), 7.22-7.27 (m, 1 H), 7.12 (d, J=16.40 Hz, 1 H), 6.76 (s, 1 H).

Example 2

D-Amino Acid Oxidase Inhibition

2.1. D-Amino Acid Oxidase Enzyme Assay

DAAO enzyme activity was measured using the substrate D-serine at its Michaelis-Menton K$_m$ of 5 mM. The rate of oxidation is measured as a rate of production of hydrogen peroxide, which was detected using the enzyme horseradish peroxidase (Sigma cat. No. P-8375). This coupled reaction uses the enzyme substrate Amplex Red (Molecular Probes), which is converted to the fluorescent reaction product, resorufin (excitation 530-560 nm; emission ~590 nm). Although DAAO has a higher pH optimum, all reagents were prepared in 50 mM sodium phosphate buffer at pH 7.4 and inhibition curves were generated at this pH.

The final concentrations of components in 200 μl total volume per well (black clear-bottom 96-well plate, Costar) were:

(a) Horseradish peroxidase: 4 Units per ml
(b) D-serine: 5 mM
(c) Test Compound: 100-0.0064 uM for IC50s
(d) Amplex Red reagent: 50 uM
(e) DMSO: 1.6%

The reactions were initiated by addition of DAAO enzyme while the fluorescence was monitored. H$_2$O$_2$ was added at 16 uM final concentration to a control well on each plate to test for compound interference with a coupled enzyme. Inhibition curves were generated in the presence of varying concentrations of the inhibitor and IC$_{50}$ values were calculated for each inhibitor.

2.2. Results of DAAO Inhibition Assay

IC$_{50}$ values were determined for selected compounds, which are summarized in Table 2 below.

TABLE 2

Human and Porcine DAAO Inhibition [IC$_{50}$]

| Compound No. | Compound Name | Human DAAO (μM) |
|---|---|---|
| 11 | 4H-furo[3,2-b]pyrrole-5-carboxylic acid | (+++) |
| 17 | 3-Phenethyl-4H-furo[3,2-b]pyrrole-5-carboxylic acid | (++) |
| 24 | 2-Benzyl-4H-furo[3,2-b]pyrrole-5-carboxylic acid | (+) |
| 26 | 3-Benzyl-4H-furo[3,2-b]pyrrole-5-carboxylic acid | (+) |
| 32 | 3-vinyl-4H-furo[3,2-b]pyrrole-5-carboxylic acid | (+++) |
| 46 | (Z)-3-(prop-1-enyl)-4H-furo[3,2-b]pyrrole-5-carboxylic acid | (+) |
| 48 | (E)-3-styryl-4H-furo[3,2-b]pyrrole-5-carboxylic acid | (+) |

IC$_{50}$ ≦ 100 nM = (+++);
IC$_{50}$ ≦ 1 μM = (++);
IC$_{50}$ ≦ 100 μM = (+)

Example 3

Chung Model Data for Compound 11

3.1. Methods

Adult male Sprague-Dawley rats, weighing 200-230 g at the time of surgery, were used. They were housed in groups of 4 in an air-conditioned room on a 12 h light/dark cycle. Food and water were available ad libitu. The animals were allowed to acclimatize to the experimental environment for three days by leaving them on a lifted metal mesh for at least 40 min. The baseline paw withdrawal threshold (PWT) was examined using a series of graduated von Frey hairs for 3 consecutive days before surgery and re-assessed on the 7th day after surgery and on the $11^{th}$ to $14^{th}$ day before drug dosing. The rat Chung model was prepared as described by Kim and Chung (1992). The rat was anaesthetized with 5% isoflurane mixed with oxygen (2 L per min) followed by an i.p. injection of sodium pentobarbitone at 50 mg/kg. The back was shaved and sterilized with 75% ethanol. The animal was placed in a prone position and a para-medial incision was made on the skin covering L4-6 level. The L5 spinal nerve was carefully isolated and tightly ligated with 6/0 silk suture. The wound was then closed in layers after a complete hemostasis. A single dose of antibiotics (Amoxipen 15 mg/rat, ip) was routinely given for prevention of infection after surgery. The animals were placed in a temperature controlled recovery chamber until fully awake before being returned to the home cage. The animals were placed in individual Perspex boxes on a raised metal mesh for at least 40 min before the test. Starting with the filament of lowest force, each filament was applied perpendicularly to the center of the ventral surface of the paw until slightly bent for 6 seconds. If the animal withdrew or lifted the paw upon stimulation, then a hair with force immediately lower than that tested was used. If no response was observed, then a hair with force immediately higher was tested. The lowest amount of force required to induce reliable responses (positive in 3 out of 5 trials) was recorded as the value of PWT. Only those animals with significant allodynia (PWT$\leq$3.5 g) were selected for drug dosing experiments. The rats in a neuropathic pain state were randomly divided into experimental groups: Vehicle group and 1 group had 8 rats and the gabapentin group had 9 rats. The drug test was carried out 12 to 14 days after surgery. Isotonic 50 mM phosphate buffer (PB), dosed orally at 3 mL/kg, served as the vehicle control. Gabapentin was dissolved in normal saline and given orally at 100 mg/kg. 1 was dissolved in PB to 10 mg/mL and given orally at 30 mg/kg. The PWT was assessed at 1, 3, 6 and 24 h following drug or vehicle administration. The animals were returned to their home cage for a break (about 30 min) between two neighboring testing time points. One-way analysis of variance (ANOVA) (SPSS software) was used for statistical analysis to compare different groups on the same time points. Paired Student -t test was used to compare different time points in the same group. The significance level was set at $P<0.05$.

3.2. Results for 4H-furo[3,2-b]pyrrole-5-carboxylic acid (11)

In rats that were dosed orally with vehicle, there were no significant changes in PWT from the baseline value over the 24-hour observation period. Gabapentin, as a positive control, orally dosed at 100 mg/kg, significantly increased the PWT, with effects commencing the first hour after oral dosing and reaching a peak 3 hours after dosing. The effect of gabapentin gradually declined from 6 hours onwards. Compound 11, at an oral dose of 10 mg/kg, also significantly elevated the PWT. Similar to gabapentin, the increase in PWT was first observed 1 hour after dosing. The effect reached a peak at 6 hours after dosing.

Example 4

Contextual Fear Conditioning Data for Compounds 11 and 1

4.1. Methods

Young-adult C57BL/6 male mice were used. Mice were received at 6-7 weeks of age. Upon arrival, mice were assigned unique identification numbers (tail marked) and were group housed in polycarbonate cages with filter tops. All mice were acclimated to the colony room for at least four weeks prior to testing and were subsequently tested at an average age of 10-12 weeks of age. During the period of acclimation, mice were examined on a regular basis, handled, and weighed to assure adequate health and suitability. Mice were maintained on a 12/12 light/dark cycle with the light on at 6:00 a.m. The experiments were always conducted during the light phase of the cycle. The day before the initiation of the experiment, mice were housed single in individual cages and maintained so till the end of the experiment. Animals were randomly assigned across treatment groups. With the exception of testing times, the mice had ad lib access to food and water. Rolipram (0.1 mg/kg) was dissolved in 1% DMSO i.p. 20 min prior to training at a dose volume of 8 ml/kg. To assess contextual conditioning, we use a standardized contextual fear conditioning task originally developed for evaluation of memory in CREB mutant mice (Bourtchouladze, R. et al.; Cell 1994, 79, 59-68). Specifically, on the training day, the mouse is placed into the conditioning chamber for 2 minutes before the onset of the unconditioned stimulus (US), a 0.75 mA foot shock of 2 seconds duration. The US is repeated two times with a 1 min inter-trial interval between shocks. Training is performed using an automated software package. After the last training trial, a mouse is left in the conditioning chamber for another 30 sec and then placed back in its home cage. Contextual memory is tested 24 hours after training. The mouse is placed into the same training chamber and conditioning is assessed by scoring freezing behavior. Freezing is defined as the complete lack of movement in intervals of 5 seconds (Kim, J. J.; Rison, R. A.; Fanselow, M. S. *Behavioral Neuroscience,* 1993, 107, 1093-1098; Phillips, R. G.; LeDoux, J. E. *Behavioral Neuroscience,* 1992, 106, 274-285; Bourtchouladze, R.; Frenguelli, B.; Blendy, J.; Cioffi, D.; Schutz, G.; Silva, A. J. *Cell,* 1994, 79, 59-68; 1998; Bourtchouladze, R.; Abel, T.; Berman, N.; Gordon, R.; Lapidus, K.; Kandel, E. R. *Learning & Memory,* 1998, 5, 365-374; _ Abel, T.; Nguyen, P. V.; Barad, M.; Deuel, T. A. S.; Kandel, E. R.; Bourtchouladze, R. *Cell,* 1997, 88, 615-626.; Kogan, J. H.; Frankland, P. W.; Blendy, J. A.; Coblentz, J.; Marowitz, Z.; Schutz, G.; Silva, A. J. *Current Biology,* 1997, 7, 1-11). Total testing time lasted 3 minutes. After each experimental subject, the experimental apparatus is thoroughly cleaned with 75% ethanol, water, dried, and ventilated for a few minutes. To evaluate the effects of compounds on contextual memory, we injected mice with a compound or vehicle 2 hours before training and trained them with 2 training trials. In parallel, a separate group of mice was injected with a reference compound, Rolipram or vehicle alone, 20 minutes before training. Mice were tested in the same context 24 hours after training.

4.2. Results

Compound 11 was dissolved in vehicle A and administered P.O. 2 hrs prior to training at a dose volume of 10 ml/kg. 10 mg/kg of 11-injected mice froze significantly more than vehicle injected mice (69.7%±3.0% and 33.3%±5.1% for a compound- and vehicle-injected, respectively; p<0.001; n=10 per dose). Similarly, Rolipram injected mice froze significantly more than their corresponding vehicle-injected mice (44.4%±4.4% vs. 27.2%±3.6% for Rolipram and vehicle, respectively; p<0.05). Importantly, there was no effect of drug-compound injections on immediate freezing responses measured 30 sec after training.

4H-thieno[3,2-b]pyrrole-5-carboxylic acid (1) was active at 10 mg/kg P.O.

All publications and patent documents cited in this application are incorporated by reference in their entirety for all purposes to the same extent as if each individual publication or patent document were so individually denoted. By their citation of various references in this document, Applicants do not admit any particular reference is "prior art" to their invention.

What is claimed is:

1. A pharmaceutical composition in an oral unit dosage form comprising, per dosage unit, a pharmaceutically acceptable carrier and a daily dosage of a compound in an amount of about 0.1 mg to about 7000 mg, said compound having the formula:

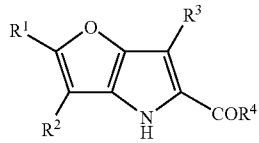

in which
$R^1$ is a member selected from the group consisting of H, and substituted or unsubstituted arylalky;
$R^2$ is a member selected from the group consisting of H, and substituted or unsubstituted arylalky; and
$R^4$ is a member selected from OH and $O^-X^+$
wherein
$X^+$ is a positive ion which is a member selected from organic positive ions and inorganic positive ions,
wherein
substituted or unsubstituted arylalkyl has the formula:

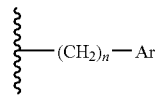

in which
Ar is substituted or unsubstituted aryl; and
n is an integer from 1 to 4.

2. The pharmaceutical composition according to claim 1 wherein said compound is present in an amount of about 50 mg to about 500 mg.

3. The pharmaceutical composition according to claim 1 wherein said oral dosage form is selected from a tablet and a capsule.

4. The pharmaceutical composition according to claim 1 comprising an amount of said compound of about 1 mg to about 100 mg.

5. The pharmaceutical composition according to claim 1 comprising an amount of said compound of about 25 mg to about 50 mg.

6. A pharmaceutical composition comprising, in single or divided oral dosage form, a pharmaceutically acceptable carrier and a daily dosage of about 0.1 mg to about 7000 mg of a compound having the formula:

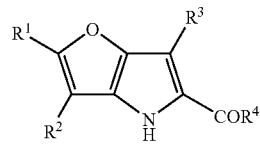

in which
$R^1$ is a member selected from the group consisting of H, and substituted or unsubstituted arylalky;
$R^2$ is a member selected from the group consisting of H, and substituted or unsubstituted arylalky; and
$R^4$ is a member selected from OH and $O^-X^+$
wherein
$X^+$ is a positive ion which is a member selected from organic positive ions and inorganic positive ions,
wherein
substituted or unsubstituted arylalkyl has the formula:

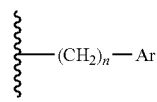

in which
Ar is substituted or unsubstituted aryl; and
n is an integer from 1 to 4.

7. The pharmaceutical composition according to claim 6 wherein said compound is present in an amount of about 50 mg to about 500 mg.

8. The pharmaceutical composition according to claim wherein said oral dosage form is selected from a tablet and a capsule.

9. The pharmaceutical composition according to claim 6 comprising an amount of said compound of about 1 mg to about 100 mg.

10. The pharmaceutical composition according to claim 6 comprising an amount of said compound of about 25 mg to about 50 mg.

11. The pharmaceutical composition of claim 1 or 6 wherein
$R^1$ is H;
$R^2$ is H; and
$R^4$ is a member selected from OH and $O^-X^+$
wherein
$X^+$ is a positive ion which is a member selected from organic positive ions and inorganic positive ions.

12. The pharmaceutical composition according to claim 11 wherein said compound is present in an amount of about 50 mg to about 500 mg.

13. The pharmaceutical composition according to claim 11 comprising an amount of said compound of about 1 mg to about 100 mg.

14. The pharmaceutical composition according to claim 11 comprising an amount of said compound of about 25 mg to about 50 mg.

15. The pharmaceutical composition according to claim 11 wherein said oral dosage form is selected from a tablet and a capsule.

* * * * *

UNITED STATES PATENT AND TRADEMARK OFFICE
CERTIFICATE OF CORRECTION

PATENT NO. : 7,579,370 B2  
APPLICATION NO. : 11/833903  
DATED : August 25, 2009  
INVENTOR(S) : Michele L. R. Heffernan et al.

It is certified that error appears in the above-identified patent and that said Letters Patent is hereby corrected as shown below:

In claim 1, column 37, lines 32 to 39, replace the structure shown with the following structure:

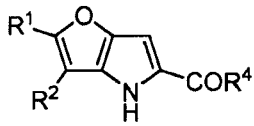

In claim 6, column 38, lines 12 to 19, replace the structure shown with the following structure:

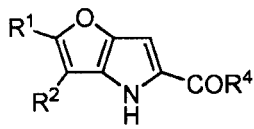

In claim 8, column 38, line 46, replace "claim" with --claim 6--.

Signed and Sealed this

Ninth Day of February, 2010

David J. Kappos  
*Director of the United States Patent and Trademark Office*